United States Patent
Katz et al.

(10) Patent No.: US 10,071,118 B2
(45) Date of Patent: Sep. 11, 2018

(54) COMPOSITIONS AND METHODS FOR TREATING PERITONEAL CANCERS

(71) Applicant: Prospect CharterCare RWMC, LLC, Providence, RI (US)

(72) Inventors: Steven C. Katz, Providence, RI (US); Richard Junghans, Boston, MA (US)

(73) Assignee: PROSPECT CHARACTERCARE RWMC, LLC, Providence, RI (US)

( * ) Notice: Subject to any disclaimer, the term of this patent is extended or adjusted under 35 U.S.C. 154(b) by 0 days.

(21) Appl. No.: 15/210,818

(22) Filed: Jul. 14, 2016

(65) Prior Publication Data

US 2017/0014452 A1    Jan. 19, 2017

Related U.S. Application Data

(60) Provisional application No. 62/193,217, filed on Jul. 16, 2015, provisional application No. 62/298,980, filed on Feb. 23, 2016.

(51) Int. Cl.
| | |
|---|---|
| *A01N 63/00* | (2006.01) |
| *A01N 65/00* | (2009.01) |
| *A61K 35/17* | (2015.01) |
| *A61K 31/10* | (2006.01) |
| *A61K 31/675* | (2006.01) |

(52) U.S. Cl.
CPC .............. *A61K 35/17* (2013.01); *A61K 31/10* (2013.01); *A61K 31/675* (2013.01)

(58) Field of Classification Search
None
See application file for complete search history.

(56) References Cited

FOREIGN PATENT DOCUMENTS

WO    WO 2014/094041 A1    6/2014

OTHER PUBLICATIONS

Gargett et al. Front. Pharma., 5-235:1-7 (2014).*
Firor et al., Exp. Biol. Medic., 240:1087-1098 (2015).*
Johnson et al., OncoImmunol., 3(7):e944059, 1-3 (2014).*
Grupp et al., NEJM, 368:1509-1518 (2013).*
Point et al., J. Immunol., 194 (1 Supplement) 143.13, May 1, 2015).*
Jayne et al (Brit. J. Surg., 89:1545-1550 (2002).*
Schott et al.,Ann. Surg., 227(3):372-379 (1998).*
Beatty et al., Cancer Immunol. Res., 2(2):112-120 (2013).*
Hoskovec et al., Acta Cirurgica Brasileira, 27(6):410-416 (2012).*
Marz et al., Gastroenterol. Report, 3(4):298-302 (2015).*
Meng et al., Can. Treat. Rev., 41:868-876 (2015).*
Wagner et al., Ann. Surg. Oncol., 20(2):1-16 (2013).*
Burkholder et al., "Tumor-induced perturbations of cytokines and immune cell networks", Biochimica et Biophysica Acta, vol. 1845, pp. 182-201 (2014).
Emtage et al., "2nd Generation anti-CEA designer t cells resist activation-induced cell death, proliferate on tumor contact, secrete cytokines and exhibit superior anti-tumor activity in vivo: a preclinical evaluation", Clin. Cancer Res., vol. 14, No. 24, pp. 8112-8122 (2008).
International Search Report and Written Opinion from International Application No. PCT/US2016/042302, 12 pages, dated Oct. 20, 2016.
Junghans, "Strategy Escalation: An emerging paradigm for safe clinical development of T cell gene therapies" J. Transl. Med., vol. 8, No. 55, pp. 1-8 (2010).
Katz et al., "Regulatory T cell infiltration predicts outcome following resection of colorectal cancer liver metastases", Ann. Surg. Oncol., vol. 20, No. 3, pp. 946-955 (2013).
Macri et al., "Hyperthermic intraperitoneal chemotherapy: Rationale and technique", World J. Gastrointest. Oncol., vol. 2, No. 2, pp. 68-75 (2010).
Nolan et al., "Bypassing immunization: Optimized design of "Designer T Cells" against carcinoembryonic antigen (CEA-expressing tumors, and lack of suppression by soluble CEA", Clinical Cancer Res., vol. 5, pp. 3928-3941 (1999).
Ottow et al., "The requirements for successful immunotherapy of intraperitoneal cancer using interleukin-2 and lymphokine-activated killer cells", Cancer, vol. 50, pp. 1465-1473 (1987).
Sugarbaker, "Technical Handbook for the Integration of Cytoreductive Surgery and Perioperative Intraperitoneal Chemotherapy into the Surgical Management of Gastrointestinal and Gynecologic Malignancy", 4$^{th}$ Edition, The Ludann Company, Grand Rapids, Michigan, 67 pages, (2005).

(Continued)

*Primary Examiner* — Thomas J Visone
(74) *Attorney, Agent, or Firm* — McDermott Will & Emery LLP

(57) ABSTRACT

The present disclosure provides compositions and methods for treating a peritoneal cancer in a subject. The methods include administering a T cell which is genetically modified to express a chimeric T cell receptor protein. The chimeric T cell receptor protein may include a T cell receptor signaling domain fused to the tumor associated antigen-binding fragment of an antibody or a T cell receptor signaling domain fused to a naturally occurring ligand which specifically binds to a tumor cell surface protein. The compositions and methods disclosed herein are therapeutically effective to reduce, for example, tumor burden, abdominal ascites, peritoneal mucin, or serum tumor marker levels.

11 Claims, 14 Drawing Sheets

Specification includes a Sequence Listing.

(56) References Cited

OTHER PUBLICATIONS

Zhong et al., "Pseudomyxoma peritonei as an intractable disease and its preoperative assessment to help improve prognosis after surgery: A review of the literature", Intract. & Rare Dis. Res., vol. 1, No. 3, pp. 115-121 (2012).
Sampson & Johnson et al. (Clin Cancer Res., 20(4):972-84, 2014).
ClinicalTrials.gov ID# NCT03054298 (First Posted: Feb. 15, 2017).
Tanyi et al. (Immunotherapy, 8(4):449-60, 2016).

* cited by examiner

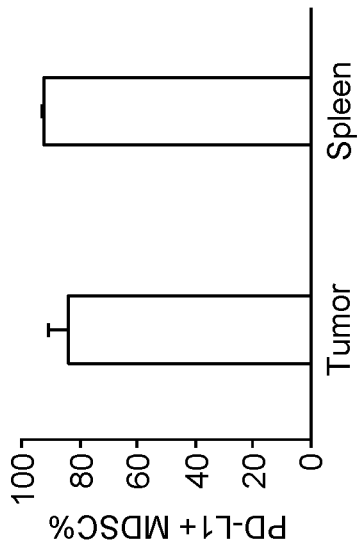
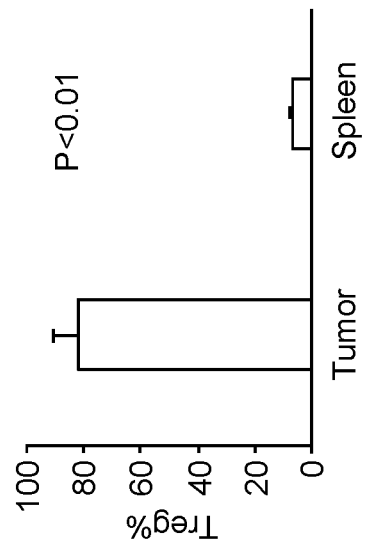
FIG. 7A
FIG. 7B
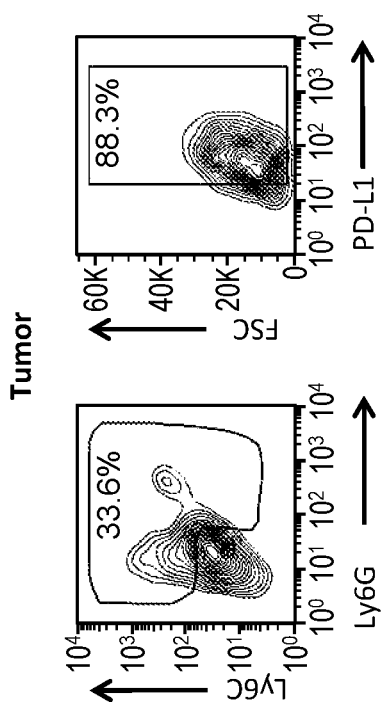
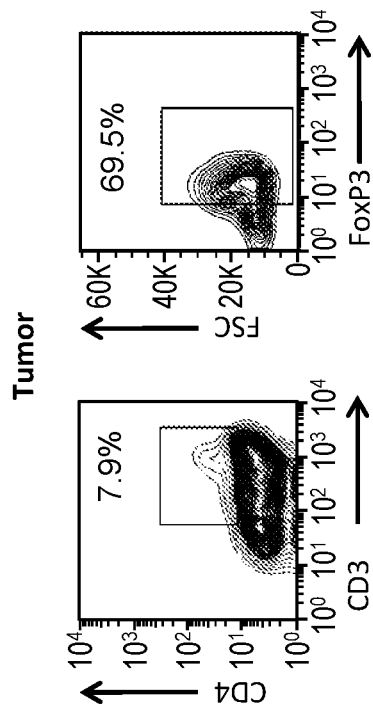
FIG. 8A
FIG. 8B

SEQUENCE LISTING

```
<160> NUMBER OF SEQ ID NOS: 1

<210> SEQ ID NO 1
<211> LENGTH: 213
<212> TYPE: PRT
<213> ORGANISM: artificial
<220> FEATURE:
```

<223> OTHER INFORMATION: Synthetic

<400> SEQUENCE: 1

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Leu Tyr Arg Ser
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210
```

COMPOSITIONS AND METHODS FOR TREATING PERITONEAL CANCERS

CROSS-REFERENCE TO RELATED APPLICATIONS

This application claims the benefit of priority to U.S. provisional application No. 62/193,217, filed Jul. 16, 2015 and U.S. provisional application No. 62/298,980, filed Feb. 23, 2016, each of which is hereby incorporated by reference in its entirety.

REFERENCE TO SEQUENCE LISTING

A Sequence Listing is being submitted electronically via EFS in the form of a text file, created Jul. 13, 2016, and named "0962010124SequenceListing.txt" (2,234 bytes), the contents of which are incorporated herein by reference in their entirety.

TECHNICAL FIELD

The subject matter described herein relates to the design and use of T cells engineered to express on its surface a receptor protein which binds a tumor antigen and which activates activities of the T cell. Methods include the intraperitoneal administration of chimeric antigen receptor T cells (CAR-T cells) to inhibit growth and/or survival of tumor cells in the peritoneal cavity.

BACKGROUND

Pseudomyxoma peritonei (PMP) and peritoneal carcinomatosis (PC) are rare diseases with an estimated incidence of 1-2 per million per year worldwide. PC affects 15% of all colorectal cancer patients at initial presentation with devastating effects (Coccolini et al, 2013, World J Gastroenterol, 19:6979-6994). These patients typically have a very poor prognosis and suffer from numerous complications of their disease, including progressive bowel obstruction. Optimal treatment involves cytoreductive surgery with hyperthermic intraperitoneal chemotherapy (CRS-HIPEC) which has been used with modest success in highly selected patients with limited disease burdens. During CRS-HIPEC, all visible intraperitoneal tumor is debulked and residual microscopic disease is treated with regionally delivered chemotherapy. CRS-HIPEC is most effective when the tumor burden is small following CRS to eliminate any tumor nodules larger than 2.5 mm. Outcomes are dependent on tumor grade, with 5-year survival rates of 63-100% for low grade, and 0%-65% for high grade disease (Sugarbaker et al., 1999, Ann Surg Oncol, 6:727-731). A randomized controlled trial demonstrated that CRS-HIPEC for patients with colorectal cancer PC resulted in significantly improved survival compared to systemic chemotherapy (Verwaal et al., 2003, J Clin Oncol, 21:3737-3743, Verwaal et al., 2008, Ann Surg Oncol, 15:2426-2432). Unfortunately, most PC patients are not candidates for CRS-HIPEC and ultimately progress and die of disease (Coccolini et al, 2013, World J Gastroenterol, 19:6979-6994; Cao et al., 2009, Ann Surg Oncol, 16:2152-2165). Even so, results with CRS-HIPEC for PC suggest that regionally delivered therapeutics are a promising approach to address this large unmet clinical need.

Immunotherapy for advanced solid tumors has gained considerable traction in recent years (Hodi et al., 2010, N Engl J Med, 363:711-723; Kantoff et al., 2010, N Engl J Med, 363:411-422; Khan et al., 2014, J Surg Res, 191:189-195; Saied et al., 2014, J Surg Res, 187:525-535). Several types of immunotherapy exist, including vaccines, antibodies, and immune cell infusions. Cellular immunotherapy for solid tumors has advanced largely through application of chimeric antigen receptor T cells (CAR-Ts). CAR-Ts are of particular interest based in part on their broad applicability since they can be produced for almost any patient and are not restricted by major histocompatibility complex types (Eshhar, 2010, Curr Opin Mol Ther, 12:55-63).

CAR-T targeting carcinoembryonic antigen (CEA) was recently tested in Phase I Hepatic Immunotherapy for Metastases (HITM) clinical trials (NCT01373047, NCT02416466) examining the safety and clinical activity of these cells against colorectal cancer LM (Katz et al., 2015, Clin Cancer Res, 21:3149-3159). As the peritoneal cavity is another common site of failure in stage IV CRC patients, it was worthwhile to test regional CAR-T delivery for PC. While regional delivery may enhance the anti-tumor efficacy of CAR-Ts, intratumoral immunosuppression will likely present additional challenges. The metastatic solid tumor microenvironment contains many immunosuppressive cell types that inhibit CAR-Ts, including myeloid-derived suppressor cells (MDSC) and regulatory T cells (Treg) (Kershaw et al., 2013, Nat Rev Cancer, 13:525-541). It has been previously shown that MDSC suppress CAR-T cells, and inhibit the antigen presentation functions of liver B cells (Thorn et al., 2014, J Leukoc Biol, 96:883-894). MDSC accomplish this immunosuppressive function through the PD-1/PD-L1 axis and IDO (Burga et al., 2015, Cancer Immunol Immunother, 64:817-829). Treg are also well studied in tumor microenvironments and have been shown to suppress CAR-Ts via PD-L1 and CTLA4 (Lee et al., 2011, Cancer Res, 71:2871-2881).

Accordingly, provided herein is a method for infusing immunoresponsive cells expressing chimeric T cell receptors to treat subjects diagnosed with PMP/PC. Data are provided which indicate that these genetically programed cells attack tumors expressing specific antigens, such as antigens expressed or specifically expressed on adenocarcinoma cells present in PMP or PC. Moreover, the data support the idea that effective IP CAR-T therapy for PC will be further enhanced through inhibition of immunosuppressive cell populations.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method of treating an intraperitoneal tumor or cancer in a subject is provided, comprising infusing into the abdominal cavity of the subject a population of genetically engineered lymphocytes which express a chimeric T cell receptor which binds to a tumor associated antigen on malignant cells in the abdominal cavity.

In some embodiments, the population of lymphocytes comprises T cells, B cells and/or NK cells. In other embodiments, the T cells comprise CD4+ cells, CD8+ cells, gamma delta T cells (γδ T cells), NK T cells and/or regulatory T cells (Treg).

In some embodiments, the chimeric receptor is comprised of the antigen-binding domain of an immunoglobulin and a T-cell receptor signaling domain. In other embodiments, the chimeric receptor is comprised of a natural ligand to a protein expressed on the cell surface of the malignant cell and a T-cell receptor signaling domain.

In some embodiments, the method comprises administering the genetically engineered lymphocytes in an amount effective to reduce the number of malignant cells in the abdominal cavity of the subject. In other embodiments, the method comprises administering genetically engineered lymphocytes in an amount effective to reduce the mass of malignant cells in the abdominal cavity of the subject. In still other embodiments, the number and/or mass of malignant cells in the abdominal cavity is measured by imaging.

In some embodiments, the method comprises administering the genetically engineered lymphocytes in an amount effective to reduce the number of malignant cells outside of the abdominal cavity of the subject. In other embodiments, the method comprises administering genetically engineered lymphocytes in an amount effective to reduce the mass of malignant cells outside of the abdominal cavity of the subject. In still other embodiments, the number and/or mass of malignant cells outside the abdominal cavity is measured by imaging.

In some embodiments, the method comprising infusing the genetically engineered lymphocytes results in a decrease in the number of peritoneal tumor cells. In other embodiments, the method results in a decrease of at least 30%, 40%, 50%, 60%, 70%, 80% or 90% of the tumor size at or before the time of the first administration of the genetically engineered lymphocytes.

In some embodiments, the method comprising infusing the genetically engineered lymphocytes results in a decrease in the size of peritoneal tumors. In other embodiments, the method results in a decrease of at least 30%, 40%, 50%, 60%, 70%, 80% or 90% of the size of the peritoneal tumors at or before the time of the first administration of the chimeric receptor T cells.

In some embodiments, the method comprising infusing the genetically engineered lymphocytes results in a decrease of at least 30%, 40%, 50%, 60%, 70%, 80% or 90% of the peritoneal volume as determined at or before the time of the first administration of the genetically engineered lymphocytes.

In some embodiments, the genetically engineered lymphocytes are infused into the abdominal cavity of the subject once every 1 week, once every 2 weeks, once every 3 weeks, or once every 4 weeks.

In some embodiments the genetically engineered lymphocytes are autologous to the subject. In other embodiments, the genetically engineered lymphocytes are not autologous to the subject.

In some embodiments, the infusing into the abdominal cavity of the subject the genetically engineered lymphocytes comprises infusing $10^6$-$10^{11}$ genetically engineered lymphocytes.

In some embodiments, the method comprises infusing a composition the genetically engineered lymphocytes and a pharmaceutically compatible solution comprising the chimeric receptor T cells in normal saline with or without 10% DMSO, wherein the total volume of the composition ranges from about 100 ml to 500 ml.

In some embodiments, the chimeric T cell receptor protein comprises an extracellular domain which specifically binds to a tumor associated antigen expressed on the surface of an adenocarcinoma, sarcoma or neuroendocrine tumor cell. In other embodiments, the adenocarcinoma, sarcoma or neuroendocrine tumor cell is present in the peritoneal cavity of the subject. In other embodiments, the adenocarcinoma, sarcoma or neuroendocrine tumor cell is present outside of the peritoneal cavity of the subject.

In some embodiments, the method further comprises infusing a second therapeutic agent into the abdominal cavity of the subject. In other embodiments, the second therapeutic agent is an immune suppressive cell inhibitor that blocks an immunoinhibitory pathway within a suppressive cell. In still other embodiments, the suppressive cell is a myeloid-derived suppressor cell (MDSC) or a regulatory T cell (Treg). In some embodiments, the second therapeutic agent inhibits immunosuppression mediated by PD-1, PD-L1, PD-L2, IDO, STAT3, GM-CSF, IL10 or TGFβ. In yet other embodiments, the second therapeutic agent is an antibody or fragment thereof that binds PD-1, PD-L1, PD-L2, IDO, STAT3, GM-CSF, IL10 or TGFβ.

In some embodiments, the infusing the second therapeutic agent is performed before, during or after the infusion of the lymphocyte which expresses a chimeric receptor protein. In other embodiments, the second therapeutic agent is infused into the abdominal cavity or intravenously.

BRIEF DESCRIPTION OF DRAWINGS

FIGS. 7A and 7B show the presence of MDSC Ly6G+ and MDSC PD-L1+ cells within IP tumor and spleen.

FIGS. 8A and 8B show the presence of Treg (FoxP3+) and CD4 T cells within IP tumor and spleen.

DETAILED DESCRIPTION

Figure 1:
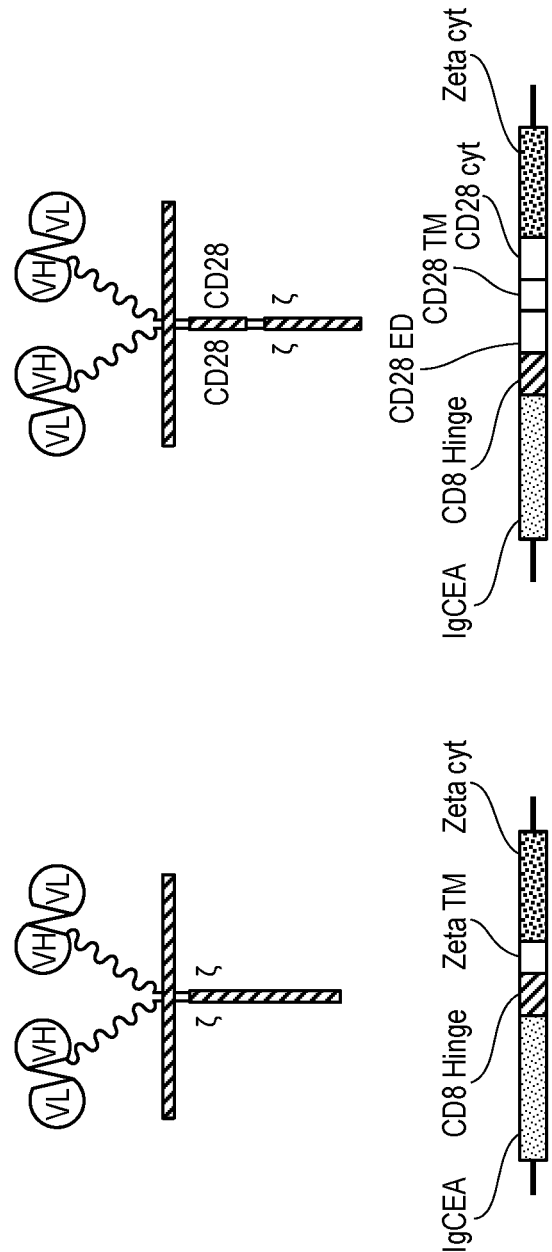
FIGS. 1A and 1B provide schematics of various anti-CEA CAR-T constructs.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The term "substantially pure" or "substantially purified" as used herein means that the CAR-T cells are as pure as it is possible to obtain by standard techniques and methods commonly known to one of ordinary skill in the art to which this invention pertains. However, a purity of 70%, 80%, 90% or greater is necessary for the monocytes to be substantially pure.

The term "peritoneal cavity" as used herein refers to the hollow or space, or a potential space, between the parietal and the visceral peritoneum.

The term "intraperitoneal cancer," "intraperitoneal tumor," "intraperitoneal malignancy" or the like as used herein refers to a malignancy including for example a tumor mass or one or more tumor cells, which is located within the peritoneal cavity. A peritoneal cancer, malignancy or tumor is a malignancy which originated in the peritoneum or peritoneal cavity.

The terms "patient," "subject," "individual," and the like are used interchangeably herein, and refer to any animal or cells thereof whether in vitro or in situ, amenable to the methods described herein. In certain non-limiting embodiments, the patient, subject or individual is a human.

As used herein the term "therapeutically effective" applied to dose or amount refers to that quantity of a compound or pharmaceutical composition (e.g., a composition comprising immune cells such as T lymphocytes and/or NK cells) comprising a chimeric receptor of the disclosure, and further comprising a drug resistance polypeptide that is sufficient to result in a desired activity upon administration to a subject in need thereof. Within the context of the present disclosure, the term "therapeutically effective" refers to that quantity of a compound or pharmaceutical composition that is sufficient to delay the manifestation, arrest the progression, relieve or alleviate at least one symptom of a disorder treated by the methods of the present disclosure. Note that when a combination of active ingredients is administered the effective amount of the combination may or may not include amounts of each ingredient that would have been effective if administered individually.

The term "chimeric receptor" as used herein is defined as a cell-surface receptor comprising an extracellular ligand binding domain, a transmembrane domain and one or more cytoplasmic co-stimulatory signaling domains in a combination that is not naturally found together on a single protein. This particularly includes receptors wherein the extracellular domain and the cytoplasmic domain are not naturally found together on a single receptor protein. The chimeric receptors of the present disclosure are intended primarily for use with T cells and natural killer (NK) cells. A chimeric receptor described herein may also be referred to herein as a chimeric antigen receptor (CAR), a chimeric ligand receptor, or a chimeric T cell receptor.

The term "tumor associated antigen" or "antigen" as used herein refers to an antigen which is specifically expressed by tumor cells or expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules.

The term "immune suppressive cell inhibitor" refers to a substance capable of reducing or suppressing the number or function of immune suppressive cells of a mammal. Examples of immune suppressive cells include regulatory T cells ("T regs"), myeloid derived suppressor cells (MDSCs), and tumor-associated macrophages.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)2, as well as single chain antibodies and humanized antibodies (Harlow et al, 1999, In: Using Antibodies: A Laboratory Manual, Cold Spring Harbor Laboratory Press, NY; Harlow et al, 1989, In: Antibodies: A Laboratory Manual, Cold Spring Harbor, N.Y.; Houston et al, 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody.

The term "antibody-derived targeting domain" "or antigen binding domain" as used herein refers to the minimum antibody fragment which contains a complete antigen-recognition and binding site. An "Fv" domain also refers to the minimum antibody fragment which contains a complete antigen-recognition and -binding site and consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The term "natural ligand" as used herein refers to a naturally occurring protein which binds specifically to another naturally occurring protein. "Natural ligand" encompasses both the full-length protein and fragments thereof which bind specifically to the same naturally occurring protein. A natural ligand as used herein can be recombinantly produced or synthetic.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein.

As used herein, the expression "specifically binds" in reference to a chimeric T cell receptor means that the chimeric T cell receptor binds to its target protein with greater affinity that it does to a structurally different protein(s).

As used herein, the expression "tumor load" or "tumor burden" refers to the number of cancer cells, the size of a tumor, or the amount of cancer in the body of a subject.

Intraperitoneal Administration of Chimeric Receptor Immune Cells

In developing therapies for treatment of disseminated tumors such as intraperitoneal tumors, it is advantageous to utilize a tumor-selective therapeutic. Immunotherapeutic cells engineered to express chimeric receptors (e.g., CAR T cells) that recognize and bind to tumor associated antigens is increasingly being proven as a promising approach to cancer treatment. Despite the ability of the engineered cells to target the tumor cells, systemic intravascular administration can nevertheless result in inadequate exposure of tumor cells to the CAR-T cells and adverse side effects due to binding of CAR-T cells to normal cells. Accordingly, it is advantageous to provide a method for administering the CAR-T cells directly to the organ or anatomic space containing the tumors. In some aspects of the present disclosure, methods are provided comprising intraperitoneal administration of chimeric receptor lymphocytes as described herein. In some embodiments, the lymphocytes are T cells.

Current CAR T therapies involve systemic infusion of the engineered cells to the patient. Such administration methods, however, may suffer from reduced concentrations of the cells at the disease site or presentation of adverse side effects due to activities of the cells. Provided herein are compositions and methods for intraperitoneal (IP) infusion of engineered immune cells to treat patients diagnosed with an intraperitoneal cancer as experiments described below show that regional IP infusion of the cells resulted in superior protection against peritoneal tumors when compared to systemically infused cells. Moreover, administration of immune pathway inhibitors to the patients receiving the IP cell (IPC) therapy further improved therapeutic efficacy for treating peritoneal metastases.

Chimeric Receptor Immune Cell Therapy

Cancer research is increasingly focused on the use of immune system components to combat malignant disease. For example, numerous therapeutic antibodies have proven successful in treating cancers and are presently marketed throughout the world. More recently, cell-based immunotherapy is emerging as a promising approach to cancer treatment in which a patient's own immune cells are engineered to recognize and attack tumors in their body. Diagnosis of a subject as having malignant tumors may include determining what tumor antigen proteins (tumor associated antigens) are expressed on the tumor cell surface. The subject can then be treated with anti-tumor immune cells which have been engineered to target and bind to the tumor associated antigen, ultimately leading to the killing of the tumor cells by the immune cell and possibly other co-administered cells or therapeutic agents. Disclosed herein are compositions and methods for treating tumors in the abdominal cavity via intraperitoneal infusion of engineered immune cells.

In one aspect are lymphocytes which have been engineered to express a chimeric receptor. The population of lymphocytes for use according to the present methods include but are not limited to T cells, B cells and NK cells. In some embodiments, the T cells comprise CD4+ cells, CD8+ cells, gamma delta T cells (γδ T cells), NK T cells and/or regulatory T cells (Treg). Of particular interest are T cells which express a chimeric receptor ("chimeric receptor T cells). The chimeric receptor immune cells are designed to bind, via the chimeric receptor protein, to diseased or malignant cells which express a cell surface protein. For example, malignant cells in the intraperitoneal cavity may express the carcinoembryonic antigen (CEA, GenBank Acc. No. NP_04354 and its related isoforms), the KIT tyrosine kinase receptor protein (GenBank Acc. No. P10721), the epithelial cell adhesion molecule protein (EpCAM; GenBank Acc. No. NP_002345 and its related isoforms), or the mucin 1 protein (MUC1, GenBank Acc. No. NP_001018016 and its related isoforms) (e.g., Yamamoto et al., 2014, J Cancer Res Clin Oncol, 140:607-612; Joensuu, 2006, Ann Oncol, 17:x280-x286; Chauhan et al., 2009, J Ovarian Res, 2:21-29; Flatmark et al., 2013, Int J Cancer, 133:1497-1506). Other examples of antigen targets expressed on cancer cells and that are currently being studied for CAR-T cell therapy include CD20 or GD2 (follicular lymphoma), CD171 (neuroblastoma), CD20 (non-Hodgkin lymphoma), CD19 (lymphoma), IL13Ra2 (glioblastoma), and CD19 (chronic lymphocytic leukemia or CLL and acute lymphocytic leukemia or ALL). Virus specific CAR-T cells have also been developed to attack cells harboring virus such as HIV. For example, a clinical trial was initiated using a CAR specific for Gp100 for treatment of HIV (Chicaybam et al (2011) Int Rev Immunol 30:294-311). It is understood that the present methods and compositions include, but are not limited to, the antigen targets listed above.

Generation of chimeric receptor proteins and immune cells expressing these proteins is well known in the art and combines the targeting function and specificity of a ligand or antibody or fragment thereof with the anti-tumor activity of an immune cell. See for example, Sadelain et al., 2013, Cancer Discov, 3:388-398. The chimeric receptor protein comprises in an N-terminal to C-terminal direction a target binding domain which specifically binds a protein expressed on the surface of a diseased target cell (e.g., a cancer cell or malignant cell present in the peritoneal cavity), a hinge domain, a transmembrane domain, and an immunomodulatory signaling domain. In some embodiments, the construct further comprises a signal peptide fused to the N-terminus of the target binding domain.

In some embodiments, the target binding domain of the chimeric receptor protein comprises the antigen-binding portion of an immunoglobulin wherein the immunoglobulin binds a protein on the surface of the diseased cell. This construct is alternatively referred to herein as a chimeric antigen receptor (CAR). The antigen binding domain can be any domain that binds to the cell surface antigen including but not limited to monoclonal antibodies, polyclonal antibodies, synthetic antibodies, human antibodies, humanized antibodies, and fragments thereof. In preferred embodiments, the antigen-binding domain of the CAR is a fragment of an antibody that is able to specifically bind the antigen when part of a CAR construct. In some instances, it is beneficial for the antigen binding domain to be derived from the same species in which the CAR will ultimately be used in. For example, for use in humans, it may be beneficial for the antigen binding domain of the CAR to comprise a fragment of a human or humanized antibody. Accordingly, in some embodiments, the antigen binding domain portion of a CAR comprises a tumor antigen binding fragment of a human or humanized antibody. In each of these embodiments, the antigen-binding domain of an antibody, such as the single-chain variable fragment (scFV or Fab) or is fused to a transmembrane domain and a signaling intracellular domain (endodomain) of a T cell receptor. Often, a spacer or hinge is introduced between the extracellular antigen binding domain and the transmembrane domain to provide flexibility which allows the antigen-binding domain to orient in different directions to facilitate antigen recognition and binding.

In some embodiments, the antigen binding moiety portion of the chimeric antigen T cell receptor targets the CEA antigen and comprises the CEA-binding domain of an antibody which has been shown to bind CEA expressed on a cell surface. The chimeric receptor construct can be generated according to methods and compositions known to the ordinarily skilled artisan. For example, a CEA CAR-T construct used in the Examples below comprises portions of the variable domain of a humanized MN14 antibody (described in U.S. Pat. No. 5,874,540, the contents of which are incorporated herein by reference it their entirety). A Fab or scFv construct can be generated from a CEA antibody according to the methods of Nolan et al. (1999, Clinical Canc Res, 5:3928-3941) to include the CEA-binding domains of the CEA antibody. In some embodiments, the CEA CAR-T construct comprises the amino acid sequence of SEQ ID NO: 1 shown below:

```
                                         (SEQ ID NO: 1)
DIQLTQSPSSLSASVGDRVTITCKASQDVGTSVAWYQQKPGKAPKLLIYW

TSTRHTGVPSRFSGSGSGTDFTFTISSLQPEDIATYYCQQYSLYRSFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC
```

In some embodiments, the CEA CAR-T construct further comprises a signal sequence at the N-terminus of SEQ ID NO:1 which is cleaved from the construct after in vivo expression of the CEA CAR-T construct. In other embodiments, the signal sequence has the sequence MGWSCIIL-FLVATATGVHS (SEQ ID NO:2). The Fab or scFv domain can then be fused to a hinge domain such as that from the CD8 hinge domain (see GenBank Acc. No. NP_001759). The hinge domain can then be fused at its C-terminus to a transmembrane domain. In one embodiment, the transmembrane domain is from the CD3 zeta chain (e.g., GenBank Acc. No. NP_000725 or from the CD28 protein (e.g., GenBank Acc. No. NP_006130). The transmembrane domain of the chimeric construct can then be fused at its C-terminus to the signaling domain of the CD3 zeta chain (e.g., GenBank Acc. No. NP_000725).

In some embodiments, the CEA-binding domain is a scFv or Fab domain from an antibody that binds CEA and the chimeric receptor construct comprises, in an N-terminal to C-terminal direction: the CEA-binding domain (e.g., SEQ ID NO:1), a CD8 hinge domain, a zeta transmembrane domain and a zeta cytoplasmic signaling domain. In other embodiments, the chimeric receptor construct comprises, in an N-terminal to C-terminal direction: the CEA-binding domain (e.g., SEQ ID NO:1), the CD8 hinge domain, a domain comprising (in an N-terminal to C-terminal direction) a portion of the CD28 extracellular domain, the CD28 transmembrane domain, and the CD28 cytoplasmic co-stimulatory domain, and a zeta cytoplasmic signaling domain.

In alternative embodiments, a known ligand to a protein expressed on the surface of a tumor cell is fused to a T cell receptor signaling domain to produce what is alternatively referred to herein as a "chimeric ligand T cell receptor" or "chimeric ligand receptor." As with CAR-T cells, T cells that express a chimeric ligand T cell receptor protein become activated in the presence of a cell expressing the target ligand receptor protein, resulting in the attack on the targeted cell by the activated T-cell in a non-MHC dependent manner. In some embodiments, a chimeric ligand receptor is specifically designed to include the extracellular domain of the KIT-ligand, a cytokine that binds to tyrosine-protein kinase KIT protein (cKIT receptor or CD117) expressed on the surface of gastrointestinal stromal tumor (GIST) cells. A chimeric T cell receptor was engineered as described in PCT Pub. No. WO 2014/121264 (see also Katz et al., J Transl Med., 2013, 11:46). The anti-KIT chimeric receptor was expressed on the surface of the T cells and the engineered cells were able to proliferate when co-cultured with KIT+ tumor cells and produce IFNγ. Moreover, mice with established GIST xenografts and treated with the anti-KIT chimeric ligand receptor T cells showed significant reductions in tumor growth rates. Accordingly, it is understood that such chimeric ligand receptor T cells can be used to treat intraperitoneal cancers according to the methods described herein. A schematic of two alternative CAR-T constructs for use in the methods as described herein are provided in FIGS. 1A and 1B.

Chimeric Receptor Intracellular Domain

The intracellular signaling domain of the chimeric T cell receptor is activated upon binding of the target antigen by the antigen-binding domain of the CAR or by the ligand portion of the chimeric ligand receptor. Generally, the domain of the endogenous CD3 T cell receptor is used as the signaling domain. More recently, however, second generation CAR molecules have been designed to further include another intracellular signaling domain from a costimulatory receptor such as CD28, 41BB, or ICOS to provide additional signals to the engineered T cell which may improve its efficacy and/or viability. Third generation chimeric T cell receptors combine multiple signaling domains or accessory regions to provide novel functionality. Accordingly in some embodiments, the cytoplasmic domain further comprises one or more co-stimulatory domains selected from the group consisting of an OX-40 costimulatory domain, an HVEM co-stimulatory domain, a 41BB co-stimulatory domain, an ICOS co-stimulatory domain, an OX40 co-stimulatory domain and a CD27 co-stimulatory domain. In one embodiment, the additional co-stimulatory domain is positioned between a CD28 co-stimulatory domain and a CD3-zeta signaling domain.

Chimeric Receptor Lymphocytes for IP Infusion

Lymphocytes engineered with chimeric receptors to enable highly specific tumor recognition and killing have gained considerable attention following promising clinical results (Grupp et al., 2013, N Eng J Med, 368:1509-1518; Porter et al., 2011, N Eng J Med, 365:725-733; Sadelain et al., 2009, Curr Opin Immunol, 21:215-223). Types of lymphocytes that can be used in the methods of the present disclosure include, without limitation, peripheral donor lymphocytes genetically modified to express chimeric receptors (Sadelain, M., et al. 2003, Nat Rev Cancer 3:35-45), lymphocyte cultures derived from tumor infiltrating lymphocytes (TILs) in tumor biopsies (Panelli, M. C., et al. 2000 J Immunol 164:495-504; Panelli, M. C., et al. 2000 J Immunol 164:4382-4392), and selectively in vitro-expanded antigen-specific peripheral blood leukocytes employing artificial antigen-presenting cells (AAPCs) or pulsed dendritic cells (Dupont, J., et al. 2005 Cancer Res 65:5417-5427; Papanicolaou, G. A., et al. 2003 Blood 102:2498-2505). The T cells may be autologous, non-autologous (e.g., allogeneic), or derived in vitro from engineered progenitor or stem cells. T cells may prepared in bulk as commonly performed with Peripheral blood lymphocytes (PBL), or tumor infiltrating lymphocytes (TILs), T cells may be purified by using, e.g. CD4, CD8, CD62L.

Genetic modification of immunoresponsive cells (e.g., T cells, CTL cells, NK cells) can be accomplished by transducing a substantially homogeneous cell composition with a recombinant DNA or RNA construct. Preferably, a retroviral vector (either gamma retroviral or lentiviral) is employed for the introduction of the DNA or RNA construct into the host cell genome. For example, a polynucleotide encoding a receptor that binds an antigen (e.g., a tumor antigen, or a variant, or a fragment thereof), can be cloned into a retroviral vector and expression can be driven from its endogenous promoter, from the retroviral long terminal repeat, or from an alternative internal promoter. Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide chimeric receptor-expressing cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells.

In yet another aspect, the disclosure is directed to pharmaceutical compositions to facilitate administration of transduced T cells as described herein to a subject in need.

The transduced T cells according to the disclosure can be made into a pharmaceutical composition or made implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed which does not ineffectuate the cells expressing the chimeric receptor. Thus, desirably the transduced T cells can be made into a pharmaceutical composition containing a balanced salt solution, preferably Hanks' balanced salt solution, or normal saline. For instance, the compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Compositions of the invention comprising genetically modified immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Those skilled in the art will recognize that the components of the compositions should be selected to be chemically inert and will not affect the viability or efficacy of the genetically modified immunoresponsive cells as described in the present invention. This will present no problem to those skilled in chemical and pharmaceutical principles, or problems can be readily avoided by reference to standard texts or by simple experiments (not involving undue experimentation), from this disclosure and the documents cited herein.

Therapeutic Methods

The present disclosure describes compositions and methods for intraperitoneal infusion of lymphocytes which express chimeric receptor T cells and which thereby target and bind malignant cells in the peritoneal cavity, leading to inhibition of tumor cell growth or death of tumor cells. Intraperitoneal administration provides a higher concentration of therapeutic agents to the tumor location to maximize therapeutic efficacy and minimize systemic toxicity of the therapeutic cells. Data provided herein shows that genetically engineered lymphocytes have significantly greater efficacy when administered via IP infusion as compared to systemic infusion. The therapeutic efficacy of these cells in enhanced by use of inhibitors of immune suppressor cells.

Therapeutic use of chimeric receptor lymphocytes involves harvesting white blood cells from a subject diagnosed with cancer, isolating and culturing the lymphocytes, transforming the lymphocytes with a vector containing the chimeric receptor gene, and administering to the subject the resultant engineered lymphocytes. Cells prepared for administration to a subject can comprise a purified population of cells, for example CD4+ T cells. Those having ordinary skill in the art can readily determine the percentage of genetically modified lymphocytes in a population using various well-known methods, such as fluorescence activated cell sorting (FACS).

The chimeric receptor T cells can be administered in any physiologically acceptable vehicle. In some embodiments, a dose of about $1\times10^6$ to $1\times10^{11}$, $1\times10^6$ to $1\times10^{10}$, $1\times10^6$ to $1\times10^9$, $1\times10^7$ to $1\times10^{11}$, $1\times10^7$ to $1\times10^{10}$, $1\times10^7$ to $1\times10^9$ or $1\times10^8$ to $1\times10^9$ cells are administered. In other embodiments, a dose of about $1\times10^6$, $1\times10^7$, $1\times10^8$, $1\times10^9$, $1\times10^{10}$, or $1\times10^{11}$ cells are administered. The precise determination of what would be considered an effective dose may be based on factors individual to each subject, including their size, age, sex, weight, and condition of the particular subject. Dosages can be readily ascertained and readily adjusted by those skilled in the art from this disclosure and the knowledge in the art. Preferable ranges of purity in populations comprising chimeric receptor T cells are about 70 to about 75%, about 75 to about 80%, about 80 to about 85%; and still more preferably the purity is about 85 to about 90%, about 90 to about 95%, and about 95 to about 100%. The cells can be administered by, for example, injection or catheter. Cells may also be administered by minimally invasive surgical techniques.

The chimeric receptor T cells are administered to the patient via intraperitoneal infusion once, twice, 3 times, 4 times or 5 times over a period of time. The period of time may be about 1 month, 2 months, 3 months, 4 months or 5 months. For example, a dose of the chimeric receptor T cells are administered once, twice, 3 times or 4 times in a one-week period. Furthermore, the one-week dosing regimen is performed every week, every other week, or 3 weeks or every month. Alternatively, the one-week dosing regimen is performed every other week. In one embodiment, the dose of the chimeric receptor T cells is administered 3 times per week, every other week. The dosing regimen is continued until the tumor load is reduced by at least 5%, 10%, 15%, 20%, 25%, 50%, 60%, 70%, 80%, 90% or 95% relative to the tumor load prior to administration of the first dose of chimeric receptor T cells.

In some embodiments, the chimeric receptor T cells are administered to a patient who has undergone debulking surgery to render the patient as disease-free as is surgically possible. Immediately following surgery, or within 1, 2 or 5 days following surgery, the patient receives intraperitoneal infusion of the CAR-T cells.

Effective chimeric receptor T cell therapy is achieved in part by determining an optimal dose of the chimeric receptor T cells. A therapeutically effective dose for chimeric receptor T cell treatment can be determined, for example, by imaging the abdomen of the patient by CT or PET scans or MRI imaging. A therapeutically effective dose will decrease the volume and/or number of malignant tumors as determined by imagine by at least 10%, 20%, 30%, 40%, 50%, 60%, 70%, 80%, or 90% or by 100%. A therapeutically effective dose would be expected to decrease the volume and/or number of malignant tumors in the abdomen within about 5 days, 1 week, 2 weeks, 4 weeks, 6 weeks or 10 weeks after the first administered dose of chimeric receptor T cells. Alternatively, a therapeutically effective dose will decrease the amount or volume of malignant ascites and/or intraperitoneal mucin by at least 10%, 20%, 30%, 40%, 50%, 60%, 70%, 80%, or 90% over the dosing period. A therapeutically effective dose will also decrease serum tumor markers if available for the targeted tumor type by at least 10%, 20%, 30%, 40%, 50%, 60%, 70%, 80%, or 90% over the dosing period.

Intraperitoneal Infusion of CEA CAR-T Cells

The efficacy of chimeric receptor T cells by IP infusion of chimeric receptor lymphocytes was shown using methods described herein. In mice treated by IP infusion of unmodified T cells or anti-CEA CAR-T cells, there was a significant reduction in tumor load as compared to animals untreated or treated with unmodified T cells. The ordinarily skilled artisan would understand that the methods described herein are useful for reducing tumor load using any chimeric receptor T cell (e.g., CAR-T cell or chimeric ligand receptor T cell) which has been engineered to specifically bind via the chimeric T cell receptor to the target protein or antigen expressed on the surface of the tumor cell.

As shown in the Examples below, direct IP infusion of CAR-Ts in mice with PC was more effective at controlling tumor than systemic infusion. CAR-Ts within peritoneal tumors were detected following IP infusion, whereas CAR-Ts were not present in peritoneal tumors following systemic injection. Treatment of malignancies using IP CAR-T infusion methods as described herein results in a reduction in adverse side effects as well.

The compositions and methods described herein are used for treating patients diagnosed with intraperitoneal tumors. The patient first undergoes diagnostic laparoscopy to lyse any peritoneal adhesions in order to ensure optimal CAR-T distribution following IP infusion of the CAR-T. This diagnostic laparoscopy can also be used to assess the disease, acquire pre-treatment cell or tissue specimens, and/or for placement of a peritoneal dialysis catheter. The IP CAR-T infusion can be performed later the same day or on a following day.

IP infusion of CAR-T comprises infusion of an initial dose of about $1\times10^9$ to $1\times10^{11}$, or about $1\times10^{10}$ cells into the peritoneal cavity. The CAR-T cells are suspended in a physiological solution such as normal saline. In some embodiments, the solution contains about 5% to 15% or about 10% dimethyl sulfoxide (DMSO). In some embodiments, immediately prior to IP CAR-T infusion, ascites fluid is drained from the peritoneal cavity. In other embodiments, aspiration is performed prior to injection of the dose of CAR-T cells to confirm the absence of blood and/or intestinal contents.

The IP infusion of a dose of CAR-T cells can be carried out manually and at room temperature. In some embodiments, the dose is infused over a time period of about 5 min to 60 min, about 30 min to 120 min, about 5 min to 30 min, about 5 min to 20 min, or about 10 min, 15 min, 20 min, 25 min, 30 min, 45 min or 60 min. The infusion can be carried out in an out-patient setting.

One or more additional doses of the CAR-T cells can be administered after the initial IP infusion. For example, an additional dose can be administered weekly, every 3 days or every 5 days wherein the additional dose is administered once, twice, or three times. In other embodiments an additional dose is administered weekly, every 3 days or every 5 days until a post-infusion assessment fails to detect malignancy in the peritoneal cavity. In some embodiments, the additional dose is equal to the initial dose. In other embodiments, each of the additional doses is about 75%, 90%, 120% or 150% of the initial dose in terms of the number of CAR-T cells. In a preferred embodiment, an additional dose of about $1\times10^{10}$ is administered to the patient IP once per week for 2 or 3 weeks.

In some embodiments, a method for treating malignancies in which tumor cells are located outside of the peritoneal cavity is provided. Studies were done to determine if IP CAR-T infusions could reduce or inhibit the growth of flank tumors in mice with synchronous PC. IP CAR-T infusions were able to significantly limit the growth of distant flank tumors while inducing marked IP responses (see Example 6). CAR-Ts were not detected within the flank tumors, suggesting that the flank tumor responses were due to IFNγ surges which were detected 4 days following IP CAR-T treatment (FIG. 7D). IP infusion of CAR-Ts with profound destruction of peritoneal tumors may have induced a phenomenon similar to the abscopal effect seen with radiation therapy (Park et al., 2015, Cancer Immunol Res, 3:610-619). Alternatively, CAR-Ts may have infiltrated the flank tumor at earlier time points. Surprisingly, systemic infusion also did not lead to a meaningful flank tumor response, which may reflect inadequate CAR-T dosing by this route, as most cells likely traffic to nodes, lung, and spleen. Importantly, the response of distant subcutaneous tumors was less durable than the response of IP tumors in accordance with the brief surge in serum IFNγ levels. Sequential regional and systemic therapy may offer improvements in efficacy for PC in the context of extra-abdominal disease. Accordingly, in some embodiments, a method of treatment is provided wherein a subject diagnosed with a peritoneal malignancy is treated with IP infusion of a chimeric receptor lymphocyte followed by treatment with systemic infusion of the chimeric receptor lymphocyte.

As PC can have a prolonged natural history, the durability of protection from IP tumor growth following IP CAR-T infusion was examined (see Example 4). Following repeated IP CAR-T dosing, mice were protected from repeat IP tumor challenge for up to 10 additional days. CAR-Ts were detectable within the PC as late as 28 days. This finding suggests persistence of CAR-Ts in the peritoneal space, potentially with the CAR-Ts acquiring effector memory features. CAR-Ts with an effector memory phenotype (CD44+CD62L-CCR7-) were detected within IP tumors in greater proportion at day 28 compared to day 10. These data suggest that following initial IP infusion, CAR-Ts undergo effector memory programming, which may have accounted for the prolonged anti-tumor protection in the peritoneal space.

Immunosuppressor Agents

Therapeutic efficacy of chimeric receptor T cell infusions is likely to be affected by factors that lead to immunosuppression, e.g., suppression of tumor-killing cells or decreased expression of anti-tumor cytokines. It is important to consider the effects of immune environment of the intraperitoneal space in the presence of a carcinoma and to treat a patient undergoing chimeric receptor T cell therapy accordingly.

The accumulation of immunosuppressive regulatory T cells (Tregs) and myeloid derived suppressor cells (MDSCs) within the tumor microenvironment represents a potential major obstacle for the development of effective antitumor immunotherapies (Weiss et al., 2014, J Immunol., 192:5821-5829). Elimination of MDSCs has been shown to significantly improve immune responses in tumor-bearing mice and in cancer patients (Ostrong-Rosenberg et al., 2009, J Immunol, 182:4499-4506); Talmadge, 2007, Clin Cancer Rres, 13:5243-5248). Provided herein are methods for inhibiting immunosuppression by, for example, Treg and MDSC, in a patient undergoing chimeric receptor T cell therapy, wherein the patient is also administered an agent which inhibits functions of immunosuppressive cells.

To examine the extent of immunosuppressive activity upon treatment with chimeric receptor T cells, Treg and MDSC were characterized in C57BL/6 mice bearing MC38 tumor cells. Specifically, Treg and MDSC are characterized in terms of their cell surface markers, cytokines and enzymes believed to play a role in suppressive activity. As shown in Example 7 below, studies showed that both MDSC and Treg could be detected within IP tumors. Both MDSC and Treg have been well described as inhibitors of endogenous T cell and CAR-T anti-tumor responses (Khaled et al., 2013, Immunol Cell Biol, 91:493-502; Burkholder et al., 2014, Biochim, Biophys Acta, 1845:182-201). IP MDSC also expressed high levels of PD-L1 (programmed death-1 receptor ligand), which was previously demonstrated to be an important mediator of CAR-T suppression (Burga et al., 2015, 64:817-829). Addition of an MDSC depletion antibody which binds Gr1 (granulocytic myeloid marker protein) or a PD-L1 blocking antibody treatment enhanced IP CAR-T performance in terms of tumor killing. The encouraging additive effects of IP CAR-T and suppressor cell targeting provide justification for combinatorial strategies in developing solid tumor immunotherapy. Accordingly, in some embodiments, a method for treating a subject diagnosed with a peritoneal cancer is provided, wherein the subject is administered a population of lymphocytes expressing a chimeric receptor as described herein via IP infusion and wherein the subject is also administered an immunosuppressing agent which suppresses the activity of suppressor T cells such as MDSCs or Tregs.

In some embodiments, the immunosuppressing agent is an antibody that binds IL10, PD-1 (programmed death-1 receptor), PD-L1 (programmed death-1 receptor ligand 1), PD-L2 (programmed death-1 receptor ligand 2), IDO (Indolamine 2,3-dexoygenase), STAT3 (signal transducer and activator of transcription 3), GM-CSF, CD25, GITR (glucocorticoid-induced TNFR-related protein), TGF-β, or CTLA4. In other embodiments, the immunosuppressing agent is administered to the subject before IP administration of chimeric receptor lymphocytes. In still other embodiments, the immunosuppressing agent is administered to the subject after IP administration of chimeric receptor lymphocytes. The immunosuppressing agent can be administered multiple times, for example, every day, every 2 days, every 3 days, every 4 days, every 5 days, every 6 days or once per week (every 7 days) after IP administration of the chimeric receptor lymphocytes. The immunosuppressing agent can be administered on the same day as the IP administration of the chimeric receptor lymphocytes. The immunosuppressing agent can be administered 1 day, 2 days, 3 days, 4 days, 5 days, 6 days, 7 days or more prior to IP administration of the chimeric receptor lymphocytes. More than one immunosuppressing agent can be administered to the patient, for example, the subject may be co-administered or serially administered antibodies which bind CD25 and antibodies which bind GR1.

Additional Therapeutic Agents

The chimeric receptor T cells of the present disclosure can be used alone or in combination with other therapies. Immunomodulatory agents may include but are not limited to interleukins, e.g. IL-2, IL-3, IL-6, IL-11, IL7, IL12, IL21, as well as the other 10 interleukins, the colony stimulating factors, such as granulocyte colony stimulating factor (G-CSF), and macrophage colony stimulating factor (M-CSF), and interferons, such as γ-interferon and erythropoietin. Other immunomodulatory agents may include monoclonal antibodies or small molecules designed to target immunoinhibitory pathways such as an antibody or fragment thereof which binds TGFβ or IL10, thereby blocking the function of TGFβ or IL10, respectively.

In a preferred embodiment, administration of the chimeric receptor T cells is coupled with administration of one or more agents as listed above which inhibit chimeric receptor T cell suppressor pathways. For example, a patient in need thereof receives intraperitoneal infusion of both chimeric receptor T cells and an agent which increases in situ viability of the chimeric receptor T cells after intraperitoneal infusion. In a preferred embodiment, the patient is administered chimeric receptor T cells and a dose of IL2. Administration of the agent which increases viability of the chimeric receptor T cells may be performed before, during or after administration of the chimeric receptor T cells.

IV. Examples

The following examples are illustrative in nature and are in no way intended to be limiting.

Example 1

Preparation of CEA CAR-T Cells

The anti-CEA scfv-CD28/CD3ζ (Tandem) chimeric antigen receptor used in the examples described herein was previously generated according to the method of Emtage et al. (2008, Clin Cancer Res, 14:8112-8122). Briefly, a tandem molecule was generated by molecularly fusing an hMN14 sFv-CD8 hinge segment of a monoclonal antibody which specifically binds CEA upstream of a construct encoding a cytoplasmic domain comprising in an N-terminal to C-terminal direction, a human CD28 extracellular domain, the CD28 cytoplasmic domain, and the ζ cytoplasmic domain. The resultant chimeric construct was cloned into a retroviral vector and verified by restriction digestion and sequencing.

For the present studies, 6-8 week old B6.SJL-Ptprca Pepcb/BoyJ (CD45.1) mice were purchased from Jackson for the purpose of generating distinguishable CAR-Ts when isolated from tissues ex vivo. Mice were housed in the animal facility at Roger Williams Medical Center in pathogen-free conditions under guidelines from the Institutional Care and Use Committee. CD45.1 mouse spleens were harvested in sterile fashion then pulverized. Red blood cells were lysed and T cells were isolated using MACS immunomagnetic bead isolation (Miltenyi). T cells were cultured in complete media with IL-2 (500 IU/mL) and anti-CD3/CD28 T-activator Dynabeads (Life Technologies) for 48 hours to achieve activation. Phoenix Ecotropic cells harboring a hMN14 sFv-CD8α-CD28/CD3ζ CAR (Emtage et al., 2008, Clin Cancer Res, 14:8112-8122) were used to produce supernatant for transduction. Activated T cells were cultured in the retroviral supernatant and underwent two spinfections. Transduced T cells were cultured and expanded in the presence of IL-2 (500 IU/mL), and CAR expression levels were checked 48 hours after transduction.

Transduction of murine splenocytes was confirmed 48 hours after transduction by measuring CAR expression on CD3+ cells using flow cytometry and an antibody which specifically binds the sFv portion of the CEA CAR-T molecule. A standard gating strategy was used to identify viable, single cells expressing CD3 and the chimeric anti-CEA CAR-T. The results showed that viral transduction efficiency was about 73% (data not shown).

Example 2

In Vitro Killing of Tumor Cells

Figure 2:
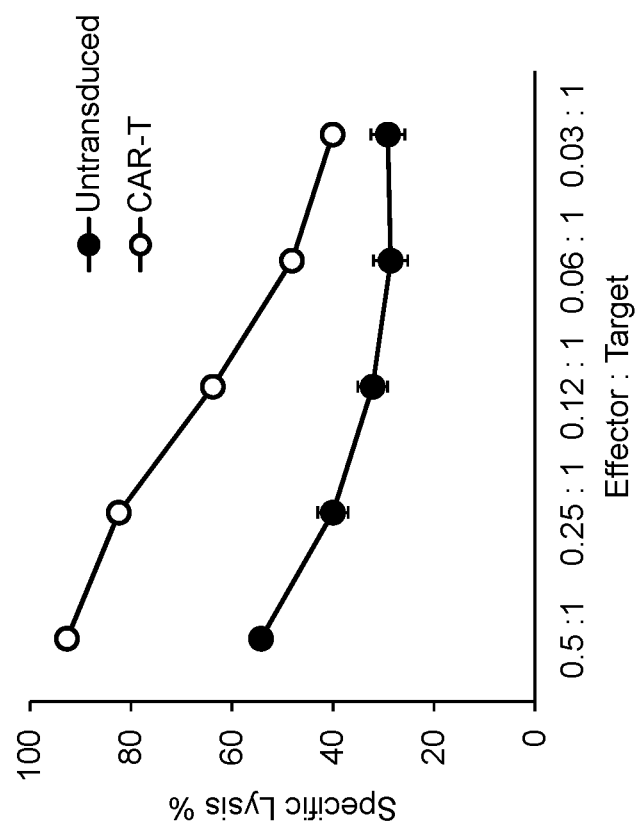
FIG. 2 shows lysis by untransduced splenic cells and chimeric receptor transduced lymphocytes.

Killing by the transduced CAR-T cells was tested in vitro using as target cells MC38 cells which were stably transfected with a gene encoding human CEA and firefly luciferase. MC38CEA+ cells were first generated by stably transfecting MC38 cells with the human CEA gene. MC38-luc was generated by transfecting MC38CEA+ cells with pLenti-III-UbC-Luciferase (Applied Biological Materials Inc, Richmond, BC Canada). Effector cells were either CEA CAR-T cells generated as described in Example 1 or untransduced splenic T cells which were used as a negative control for the effector cells. Bioluminescence assays were performed in which CAR-Ts or untransduced T cells were co-cultured with MC38CEA-luc at various Effector:Target ratios. Effectors were cultured in complete media with IL-2 (500 IU/mL) prior to the assays. Cells were plated in complete media in 96 well optical plates at varying Effector:Target ratios and incubated overnight. After incubation, media was discarded and luciferin (150 μg/mL) was added to the wells. Plates were analyzed in an IVIS 100. Supernatants were collected and measured for luminescence activity and Specific Lysis % was calculated as 100×[(experimental killing−spontaneous luminescence)/(maximal killing−spontaneous luminescence)]. As seen in FIG. 2, transduced CAR-T cells caused lysis at a significantly higher rate than untransfected cells. At an Effector:Target ratio as low as 0.03:1, specific lysis was 40% and significantly higher than activated untransduced T cells (p=0.02).

Example 3

CAR-T Cell Delivery and Killing of Tumor Cells

To show that IP delivery improves CAR-T efficacy in mice with peritoneal cancers (PC) compared to systemic tail vein (TV) infusion, both infusion methods were studied in mice with established IP tumors. Mice harboring CEA+ PC were generated by the IP injection of the MC38CEA-luc cells.

Six to eight week old C57B1/6J mice were purchased from Jackson Laboratories (Bar Harbor, Me.) and were used in all in vivo models. Mice were injected intraperitoneally with $2.5 \times 10^6$ MC38CEA-luc cells on day 0 using a 26 gauge×½" needle attached to a 1 ml syringe. Cells had been resuspended in normal saline for injection and the injection was performed at room temperature. The needle traverses the midline fascia 2-3 mm superior to the pubic symphysis and aspiration was performed prior to injection to confirm absence of blood or intestinal contents. In vivo work was carried out over the span of 14 days. On days 3 and 6, tumor-bearing mice were treated with CAR-Ts ($2.5 \times 10^6$ cells), either via IP or TV infusion. All mice were administered IL-2 (1000 IU/injection) daily beginning with the first CAR-T injection on day 3. Control mice were treated with untransduced splenic cells on days 3 and 6 or treated with IL-2 alone. For the bioluminescent mice were imaged on an IVIS 100 imaging station (Caliper Life Sciences) on even days during in vivo studies after being injected with 200 µL of 15 mg/mL luciferin.

Figure 3A:
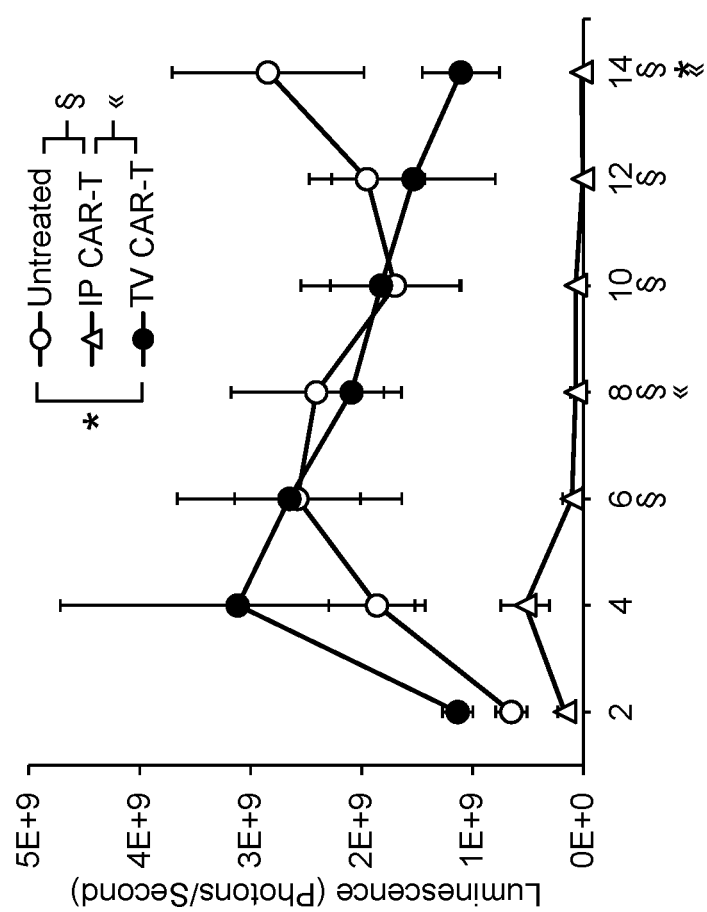
FIG. 3A shows luminescence in animals harboring tumors and which had been administered chimeric receptor transduced lymphocytes by intraperitoneal (IP) or tail vein (TV) injections.
Figure 3B:
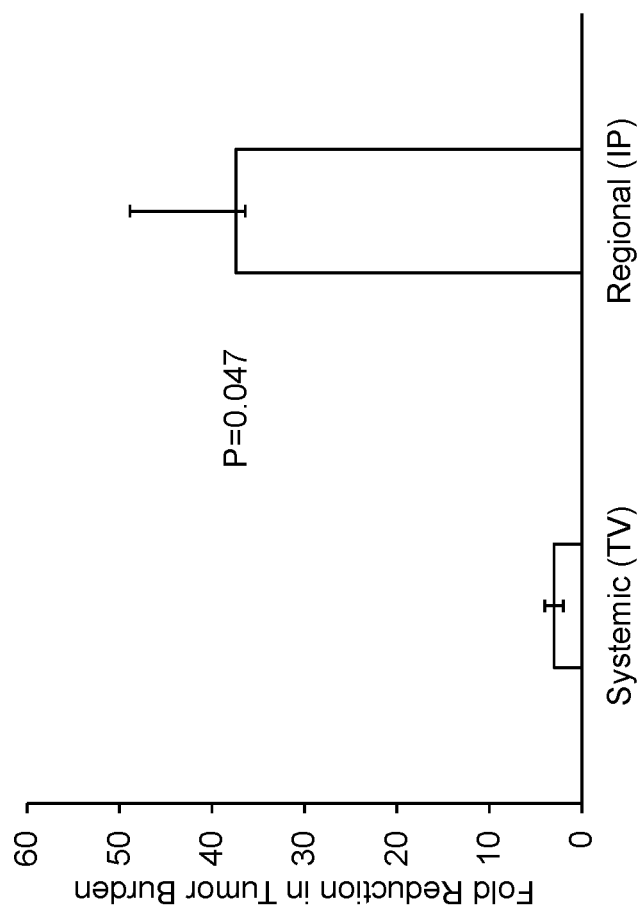
FIG. 3B shows reduction in tumor volume in animals harboring tumors and which had been administered chimeric receptor transduced lymphocytes by intraperitoneal (IP) or tail vein (TV) injections.

Data are presented in FIGS. 3A and 3B. In FIG. 3A each line on the plot is representative of the average of 4 mice. Fold reduction in tumor luminescence was calculated between days 4 and 14 of the in vivo study, comparing TV to IP CAR-T delivery and the results are shown in FIG. 3B. Error bars in FIGS. 3A and 3B are representative of SEM values. P values were calculated using Student's t test.

A single treatment of regionally delivered IP CAR-Ts resulted in significantly reduced tumor burden (p<0.01), and this remained significant compared to untreated animals at each subsequent time point. IP infusion of CAR-Ts remained more efficacious than systemic TV CAR-Ts for up to 8 days following the second CAR-T treatment. In contrast to IP CAR-Ts, TV CAR-Ts did not have a significant impact on tumor growth until day 14 when compared to untreated animals (p=0.04). IP CAR-T treated mice exhibited a 37-fold reduction in tumor burden between days 4 and 14, whereas TV CAR-T treated mice exhibited only a 3-fold reduction in tumor burden over the same time period (p=0.05) (FIG. 3B). In 4 mice treated with regionally delivered IP CAR-Ts, there was no detectable tumor upon necroscopy at day 14. Microscopic tumor was, however, still detectable by bioluminescence monitoring on the same day. In contrast, all of the TV treated animals had grossly visible IP tumor upon necroscopy.

Example 4

Durable Protection by CAR-T Cells

Having confirmed that IP CAR-T infusions are superior to systemic administration, studies were performed to assess the durability of the protection against IP tumor challenge. Following IP CAR-T infusion treatment, mice were re-challenged with IP tumor injections and tumor progression was monitored by bioluminescence. In this study, mice received CAR-Ts on days 2, 4, 6 and 8, and received a rechallenge dose of $2.5 \times 10^6$ MC38CEA-luc on Day 10. Tumor growth was measured by bioluminescence as described in Example 3.

Figure 4A:
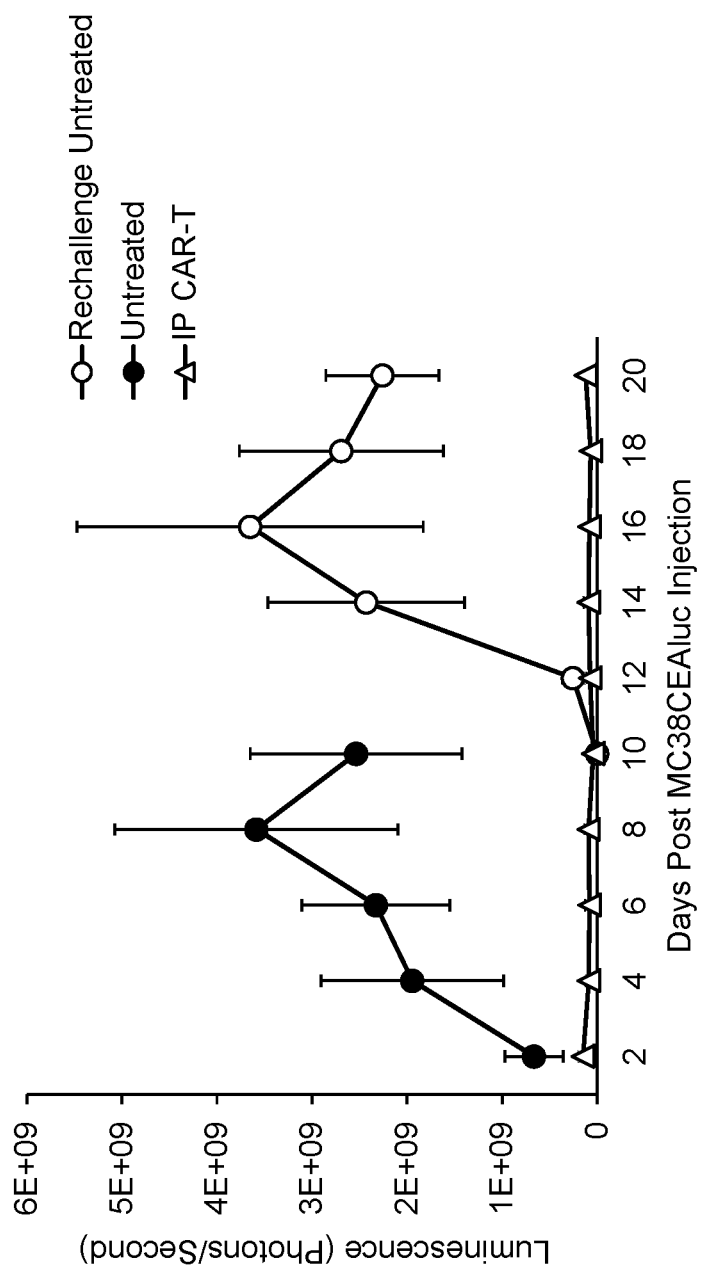
FIG. 4A shows luminescence in animals harboring tumors which had been treated with chimeric receptor transduced lymphocytes by intraperitoneal (IP) or tail vein (TV) injections and which were rechallenged with tumor cells.
Figure 4C:
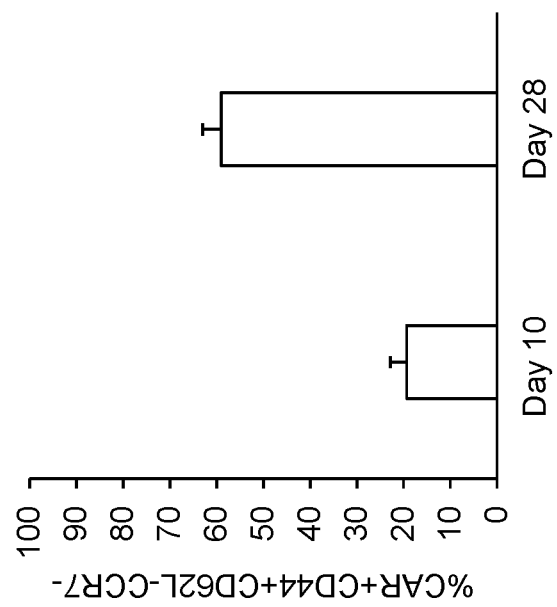
FIGS. 4B and 4C show infiltration of tumors in vivo by leukocytes expressing the chimeric receptor protein (FIG. 4B) or by leukocytes having an effector memory phenotype (FIG. 4C).
Figure 4B:
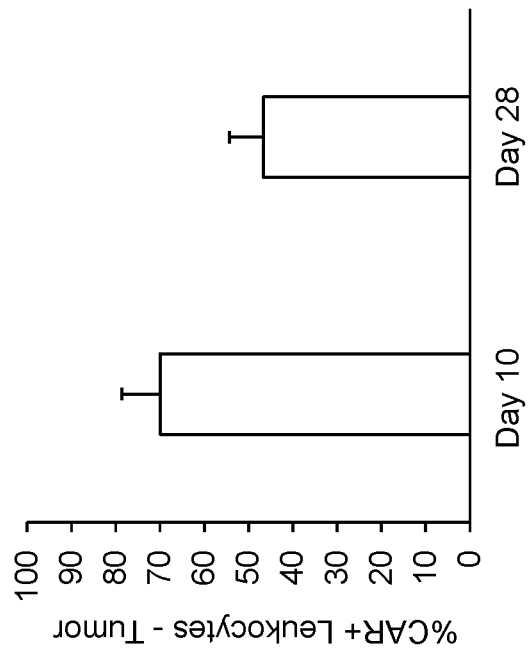

Mice that had received prior CAR-T IP infusions demonstrated a significant decrease in tumor growth compared to mice with no prior CAR-T treatment (p=0.02). Protection from IP tumor growth extended for up to 10 days following tumor re-challenge (p=0.01) (FIG. 4A). The frequencies of CAR+ lymphocytes recovered from IP tumor tissue at both day 10 (n=5) and day 28 (n=3) time points were compared. Small amounts of visible tumor were harvested and CAR-Ts were found to comprise 69% of intratumoral leukocytes on day 10, and 47% on day 28 (FIG. 4B). Memory phenotypes of CAR+ phenotypes were examined at both day 10 (n=5) and day 28 (n=3) time points using flow cytometry in which intratumoral CAR-Ts were immunophenotyped. A standard gating strategy was used with antibodies to CD62L (MEL-14, BD Bioscience), CCR7 (4B12, BD Bioscience) and CD44 (IM7, BD Bioscience). An increase in the proportion of CAR-Ts with an effector memory phenotype (CAR+ CD44+CD62L-CCR7-) was detected in the intratumoral CAR-T cells (FIG. 4C), suggesting that following initial IP infusion, CAR-T cells undergo effector memory programming.

Example 5

Protection Against Extra-Abdominal Tumor Growth by IP CAR-T Infusion

Considering that patients with IP tumors may have disease at other anatomic sites, studies were performed to determine if IP CAR-T infusions protected against subcutaneous flank tumor growth. Mice were simultaneously injected with $1.0 \times 10^6$ MC38CEA-luc cells IP and in the left flank. Flank tumor size was measured in two dimensions (mm$^2$) with calipers. Mice were imaged on an IVIS 100 on even days during in vivo studies, after being injected with 200 µL of 15 mg/mL luciferin as described in Example 3.

Figure 5A:
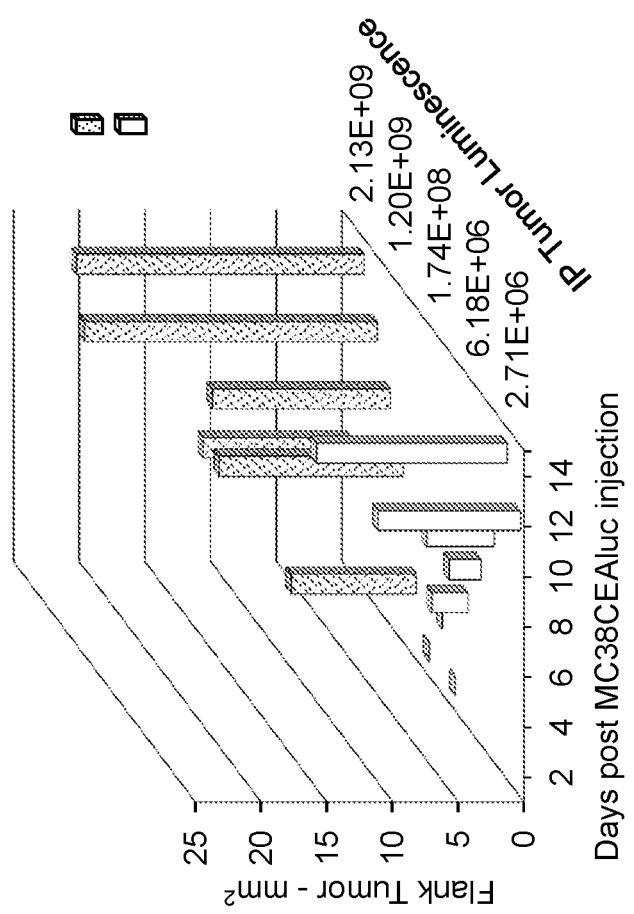
FIG. 5A illustrates therapeutic efficacy of IP chimeric receptor T cell infusion on tumors outside of the peritoneal cavity.
Figures 5B, 5C:
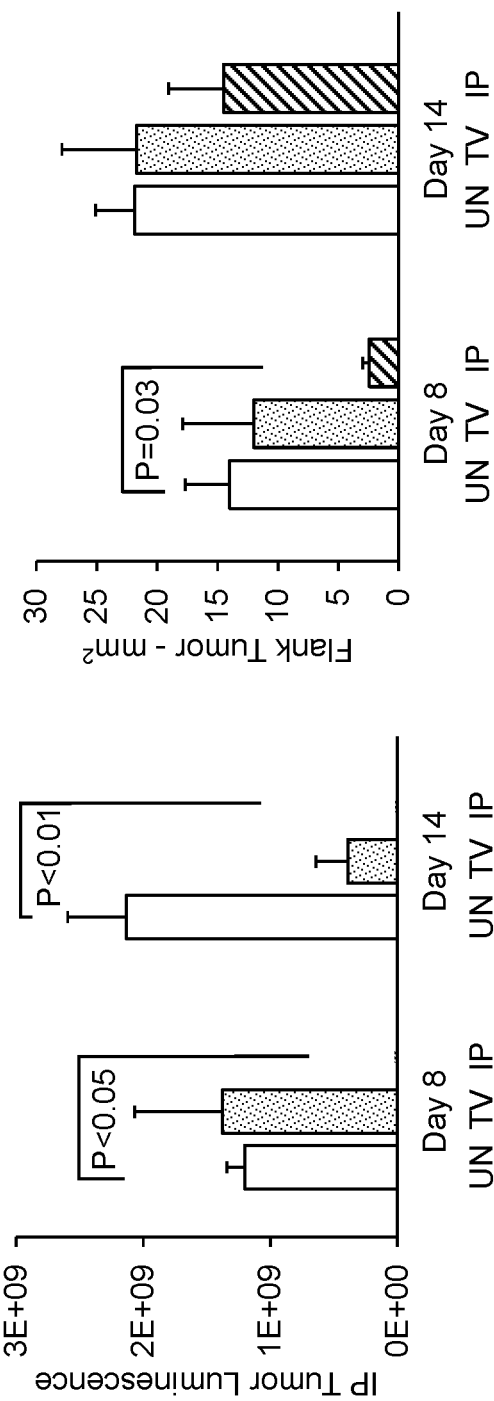
FIG. 5B shows IP tumor reduction via bioluminescence after TV vs. IP administration of chimeric receptor T cells.
FIG. 5C shows reduced flank tumor burden via measurement with calipers after TV vs. IP administration of chimeric receptor T cells.
Figure 5D:
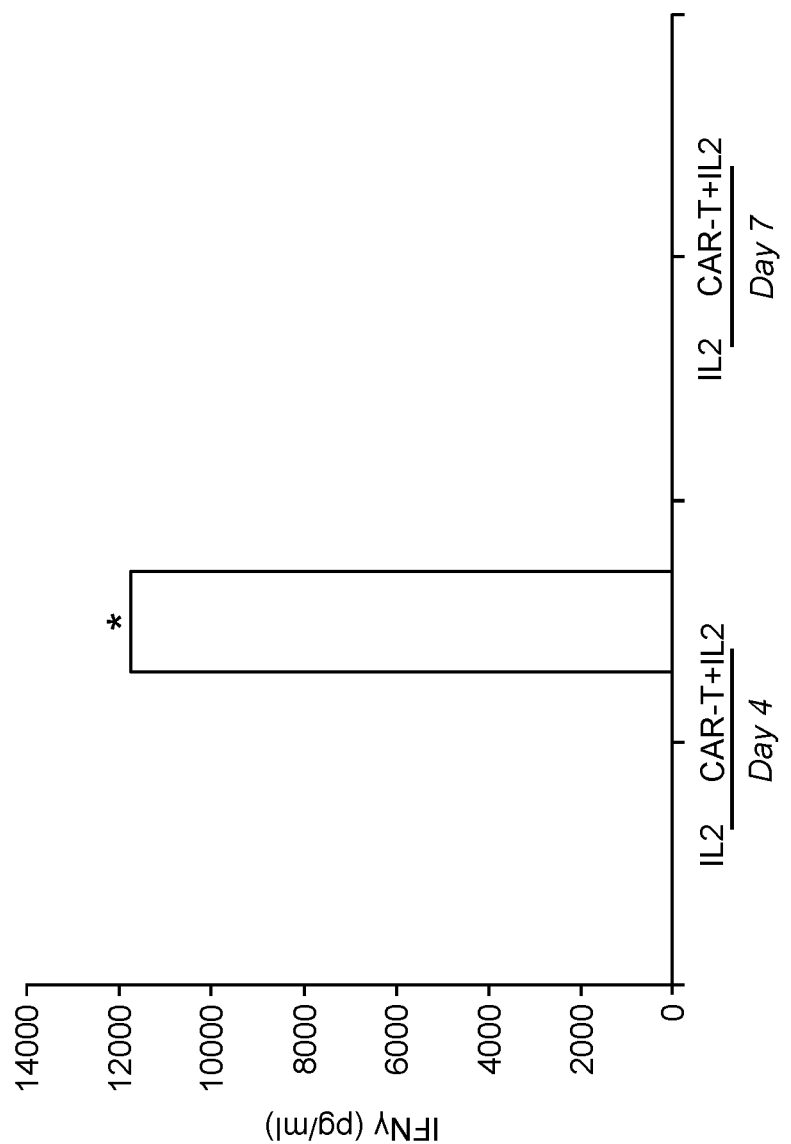
FIG. 5D shows systemic IFNγ levels after IP administration of chimeric receptor T cells.

Following two treatments on days 3 and 6, IP CAR-Ts led to decreased IP and flank tumor burden compared to untreated animals (p<0.05), as well as animals receiving untransduced splenic T cells (data not shown). Tumor reduction also trended favorably when compared to mice that received CAR-Ts via TV and mice that received IL-2 support only. This corresponded with a significantly less flank tumor area in IP CAR-T treated mice when compared to untreated animals on the same day (p=0.03, FIGS. 5A, 5B and 5C). CAR-Ts were not recovered after flow cytometry staining for trafficking in whole blood, flank tumor tissue, or left inguinal lymph nodes. However, IP CAR-T infusions did lead to high levels of systemic IFNγ at 4 days following treatment (FIG. 5D).

Example 6

IP Tumor Infiltration by Immunosuppressive Cells

Although IP CAR-T infusions mediated durable responses in mice with PC, it was worthwhile to consider that immunosuppressive cells could limit CAR-T function. MDSC and Treg, which we have previously shown to suppress CAR-Ts in colorectal cancer LM models (Burga et al., 2015, Cancer Immunol Immunother, 64:817-829), were detected within IP tumors.

Tumor leukocyte contents were immunophenotyped using flow cytometry as described in Example 3 to detect the presence of suppressive cell populations. Antibodies used for these surface markers: CD4 (RM4-5, BD Bioscience), CD11b (M1/17, BD Bioscience), Ly6C (AL-21, BD Bioscience), Ly6G (1AB, BD Bioscience), PD-L1 (MIH5, BD Bioscience). Intracellular FoxP3 staining was performed with Mouse FoxP3 Permeabilization Kit (BD Bioscience). Single stain and isotype controls were used for each experiment. Analysis of acquired flow samples was performed with FlowJo software (Tree Star Inc., Ashland Oreg.).

Figures 6A, 6B:
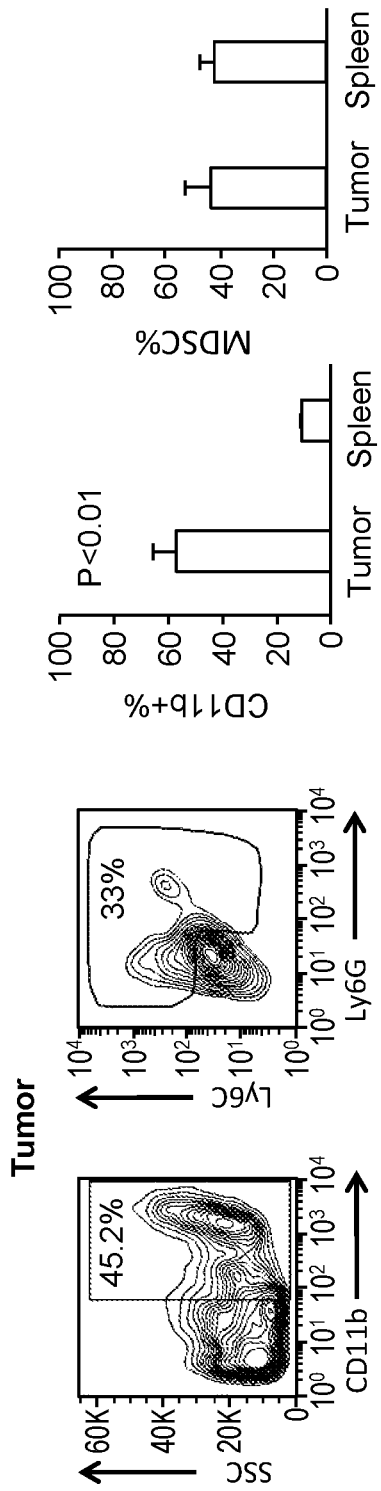
FIGS. 6A and 6B show the presence of CD11b+ and MDSC (Ly6G+) cells within IP tumor and spleen.

Tumor leukocyte contents were immunophenotyped to detect the presence of suppressive cell populations. MDSC were found in the tumors after staining for CD11b, Ly6C and Ly6G. Representative dot plots show MDSC from the IP tumors, along with bar graphs comparing MDSC populations from the tumors and spleens of the same untreated animals. The percentages of CD11b+ cells among all live cells and MDSC (Gr-1+) among CD11b+ cells are shown in FIGS. 6A and 6B). MDSC were also immunophenotyped for the expression of the immunosuppressive marker PD-L1 (FIGS. 7A and 7B). Representative tumor dot plots show that Treg, expressed as the percentage of FoxP3+ cells among CD3+CD4+ T cells, were also found within the IP tumors. Smaller populations were found within the spleens of the same animals (FIGS. 8A and 8B). Bars are representative of 3 mice per group. Error bars are representative of SEM values. P values were calculated using Student's t test.

On average, CD11b+ cells represented 57% of leukocytes in IP tumors, compared to 11% from the spleens of the same animals ($p<0.01$). Both Ly6G+ granulocytic MDSC (gMDSC) and Ly6C+ monocytic MDSC (mMDSC) were found within IP tumor (43%) and spleen (41%) (FIGS. 6A and 6B). The immunosuppressive marker PD-L1 was expressed on both MDSC subsets, and was expressed at equally high levels, whether they were derived from the tumor or the spleen (FIGS. 7A and 7B). Treg (FoxP3+) were found to comprise 82% of CD4 T cells within the tumors, compared with 7% in spleens from the same animals ($p<0.01$) (FIGS. 8A and 8B).

Example 7

CAR-T Administration Combined with Suppressor Cell Depletion

Tests were performed to study the potential therapeutic efficacy of IP CAR-T infusions in combination with suppressor cell depletion or blockade of the PD-1/PD-L1 immunoinhibitory pathway. IP CAR-Ts combined with depleting antibodies against MDSC and Treg, or blocking antibodies against the PD-L1 pathway, were administered to mice that had been injected with MC38CEA-luc. The depleting antibodies administered were anti-PD-L1 and anti-Gr1 antibodies (which bind the PD-L1 and Gr1 proteins on the surface of MDSCs) and anti-GITR antibodies (which bind the GITR protein on the surface of Treg cells). Tumor reduction was monitored by bioluminescence over 14 days as described in Example 3.

Figures 9A, 9B:
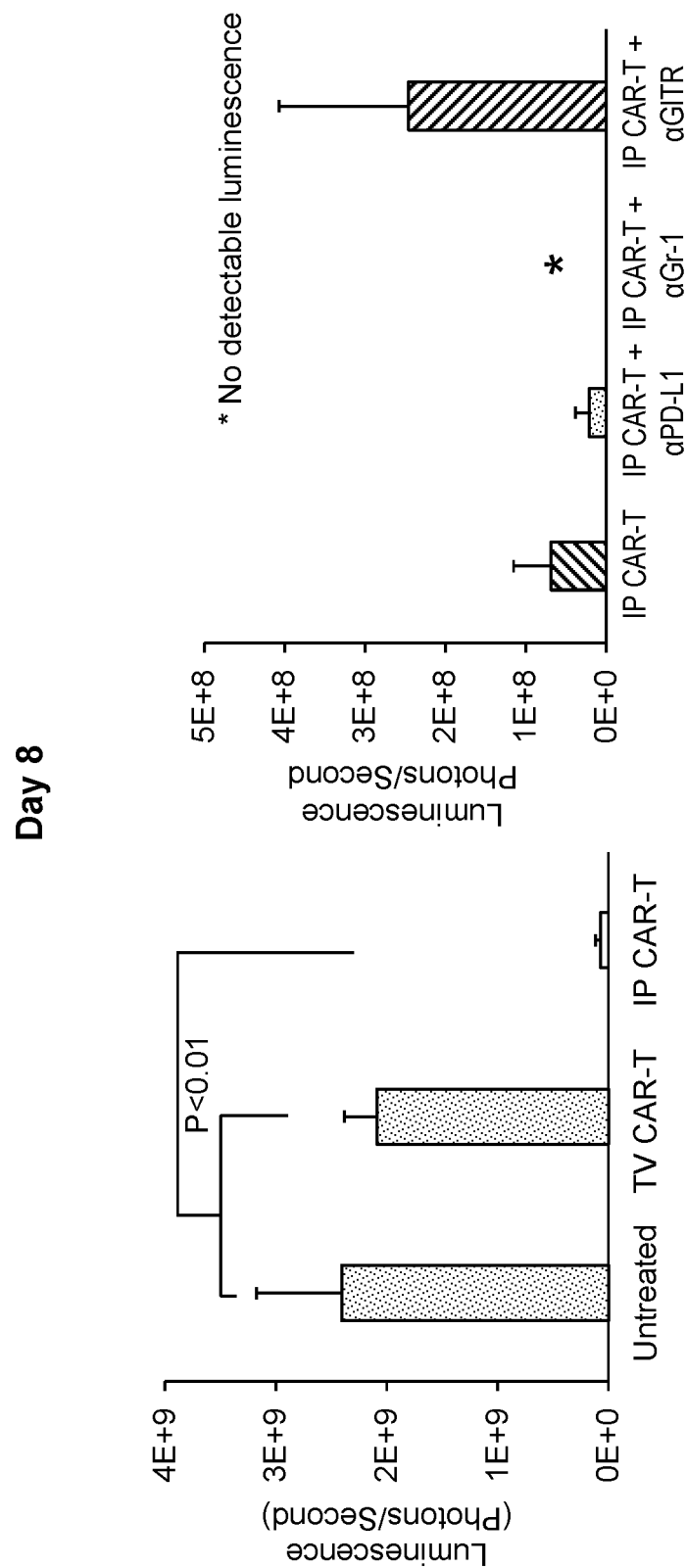
FIG. 9A shows the effects of TV and IP chimeric receptor T cell infusion on tumor burden on Day 8 after infusion.
FIG. 9B shows the effects of administration of antibodies that bind PD-L1, Gr-1 or GITR on efficacy of IP chimeric receptor T cell infusion on Day 8 after infusion.
Figure 10A:
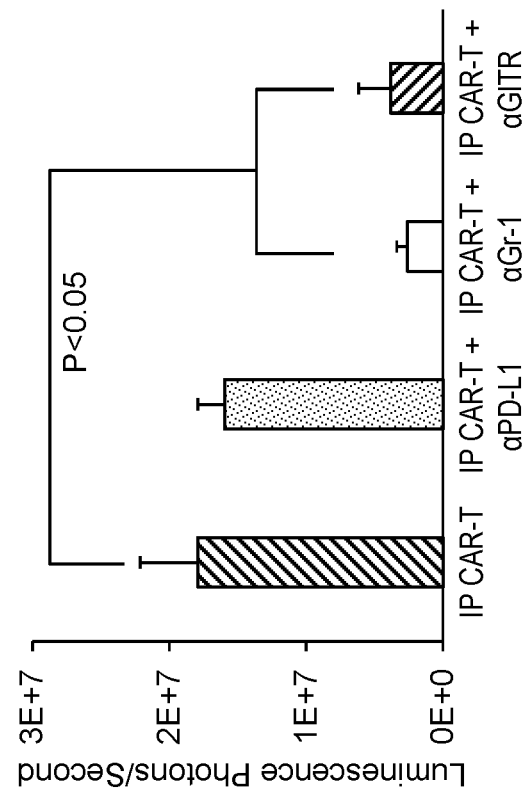
FIG. 10A shows the effects of TV and IP chimeric receptor T cell infusion on tumor burden on Day 14 after infusion.
Figure 10B:
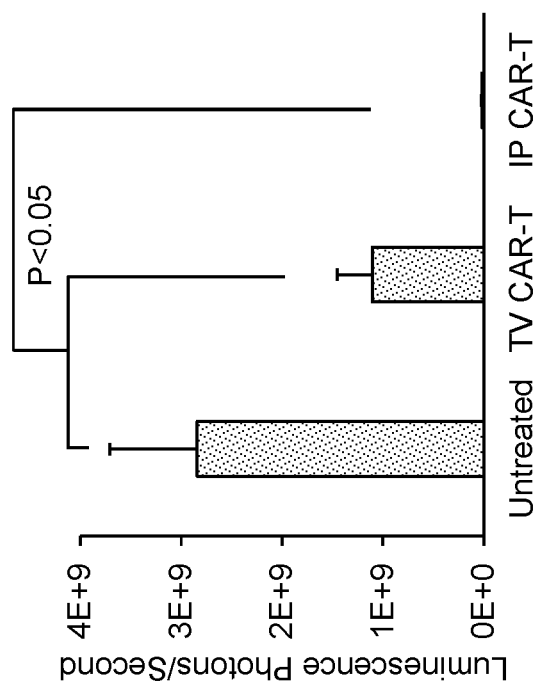
FIG. 10B shows the effects of administration of antibodies that bind PD-L1, Gr-1 or GITR on efficacy of IP chimeric receptor T cell infusion on Day 14 after infusion.

Bar graphs compare the efficacy of regional IP CAR-Ts to systemic TV CAR-Ts (FIG. 9A), and IP CAR-Ts alone to IP CAR-Ts with antibodies on day 8 after the treatments (FIG. 9B) and the efficacy of regional IP CAR-Ts to systemic TV CAR-Ts (FIG. 10A), and IP CAR-Ts alone to IP CAR-Ts with antibodies at the end of the study on day 14 (FIG. 10B). Bars are representative of 4 animals per group. Error bars are representative of SEM values. P values were calculated using Student's t test. Gross inspection images and bioluminescence images were analyzed as well (data not shown).

Figure 11:
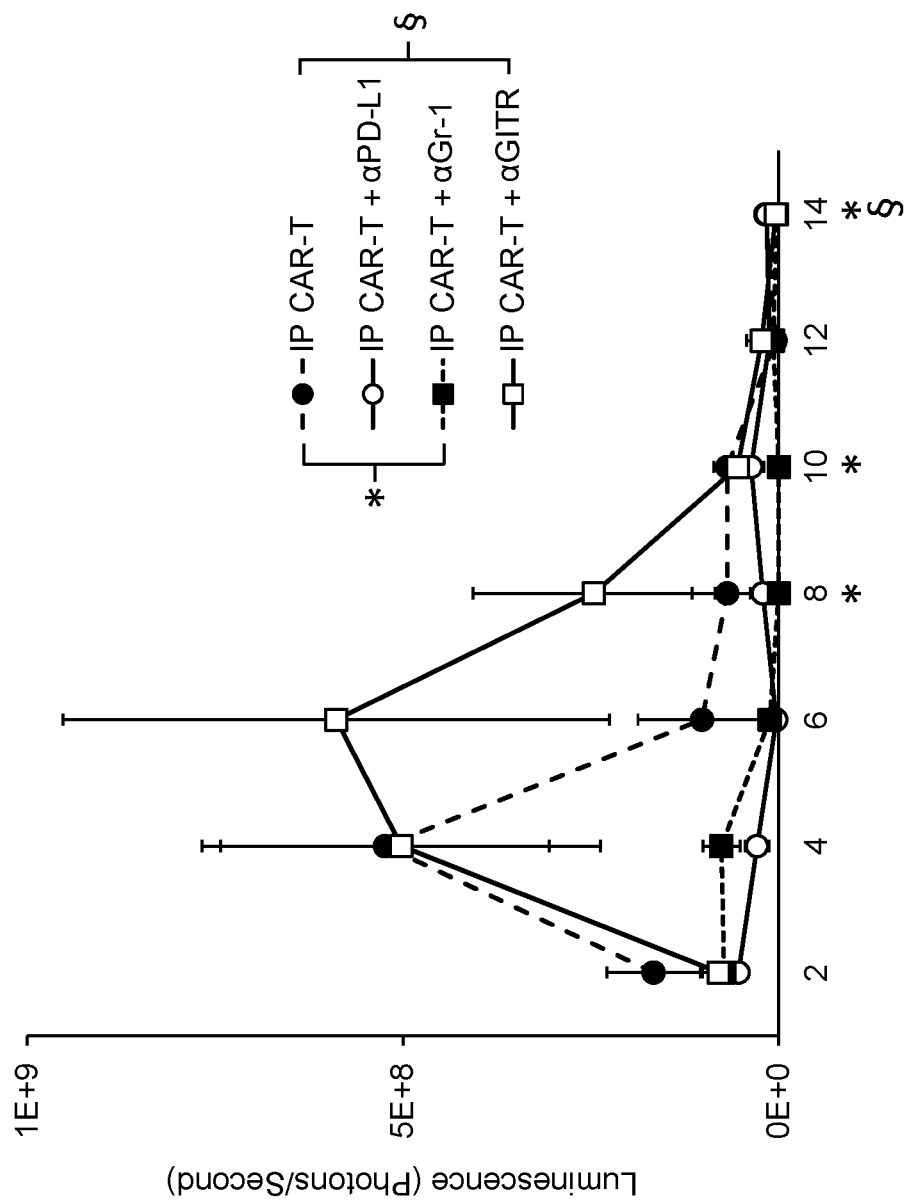
FIG. 11 shows the effects of administration of antibodies that bind PD-L1, Gr-1 or GITR on efficacy of IP chimeric receptor T cell infusion over a 14-day period after infusion.

IP CAR-Ts alone, and when used in combination with anti-PD-L1, anti-Gr1, or anti-GITR antibodies, resulted in significant reductions in tumor burden compared to untreated animals. On day 14, CAR-Ts alone significantly diminished tumor burden when compared to untreated mice, mice that received untransduced T cells, and mice that received daily dose IL-2 alone (FIG. 10A, $p<0.05$). CAR-Ts combined with the depletion of Treg showed even further reduced burden from CAR-Ts alone (FIG. 10B, $p<0.01$), as did the combination of CAR-Ts and MDSC depletion ($p=0.017$) (FIGS. 10A and 10B). Tumor burden was measured through day 14 with results shown in FIG. 11. The combination of CAR-Ts and anti-Gr-1 was the most efficacious overall, showing no detectable bioluminescence on days 8 and 10. On day 14, there was no detectable tumor found in any mouse that received IP CAR-T upon gross inspection (data not shown).

Example 8

Patient CAR-T Cell Production

Leukapheresis is performed at a validated blood center. CAR-Ts are prepared at a Good Manufacturing Practice (GMP) facility with standard operating procedures (SOPs) for processing, manufacturing, expansion, dose harvesting, labeling, storage and distribution. Briefly, patient peripheral blood mononuclear cells (PBMCs) are isolated from leukapheresis product using Ficoll. PBMCs are then activated for 48-72 hours in tissue culture flasks containing AIM V media (Life Technologies, Grand Island, N.Y.) supplemented with 5% sterile human AB serum, 50 ng/mL of anti-CD3 monoclonal antibody and 300-3000 U/mL of IL2.

Using the spinoculation method (e.g., Quintas-Cardama et al., 2007, Hum Gene Ther, 18:1253-1260), $7.2-14.4 \times 10^8$ T cells are transduced in retronectin coated 6-well plates in AIM V media with 5% human AB serum, 3000 U/mL of IL2, and protamine at low speed centrifugation for 1 hour at room temperature. The transduction step is carried out a total of two-three times over 24-hrs. After transduction, cells are washed in media and incubated for 48-72 hours at 37° C. CAR-Ts are further expanded in Lifecell tissue culture bags (Baxter, Deerfield, IL) for 10-14 days. CAR-T growth curves and cell viability are examined periodically and cell growth media is replaced as required. CAR-Ts are examined by flow cytometry with fluorescently labeled antibodies specific for CD3, CD4, CD8, and anti-CAR antibodies. Flow cytometry is performed on a CyAn (Beckman Coulter, Brea, Calif.) or LSR-II (BD Biosciences, San Jose, Calif.) machine. In vitro activity of patient products is measured by bioluminescence cytotoxicity assay. Luciferase-expressing tumor cells with the appropriate target are mixed with specific CAR-T at various ratios in 96-well round bottom plates and loss of bioluminescence from each well is measured (Karimi et al., 2014, PLoS One, 9:e89357).

Clinical doses are prepared using a Fenwal cell harvester system (Baxter, Deerfield, Ill.) in freezing media containing PlasmaLyte (Baxter), 20% human bovine albumin, 10% DMSO and IL2. Bacterial and fungal cultures are monitored for 14 and 28 days respectively. Assays for bacterial endotoxin are performed using LAL Endotoxin assay kits (Lonza, Walkersville, Md.). The clinical dose is stored in liquid nitrogen and thawed immediately prior to infusion.

Example 9

Dose Determination in a Mouse Model

Animal studies are performed to identify a minimal dose of CAR-T cells necessary to achieve killing of IP tumor cells. A murine model of carcinomatosis is generated by injecting C57BL/6 mice with tumor antigen-expressing tumor cells. The antigen-expressing tumor cells are produced from the MC38 cell line, a colorectal carcinoma cell line derived from primary mouse colon carcinoma (Rosenberg et al., 1986, Science, 233:1318-1321). MC38 cells are transduced with full length human antigen cDNA using a retroviral expression vector. The MC38 cells are also stably transfected with a luciferase gene. C57BL/6 mice are injected intraperitoneally with $2.5 \times 10^6$ murine colorectal carcinoma cells. Seven days after injection of the tumor cells, the mice are infused with $2.5 \times 10^6$, $10^7$, or $10^8$ specific CAR-T cells using a needle inserted directly into the peritoneal cavity. Each mouse receives a subcutaneous injection of IL2 (200 µl of 1.5 µg/mL) each day following the CAR-T infusion.

After infusion of the CAR-T cells, the mice are monitored for tumor growth and response to treatment by measuring bioluminescence using, e.g., an IVIS system (PerkinElmer). To assess extraperitoneal or off-target CAR-T delivery, flow cytometry is performed on peripheral blood, liver, lung, kidney, colon, and stomach to measure the frequency of CAR+ T cells at these sites. Animal survival is also carefully monitored and charted.

Example 10

Duration of CAR-T Persistence and Multiple CAR-T Infusions

If mice treated according to the study described in Example 3 fail to achieve a complete response to a single IP CAR-T infusion, studies are done to determine the duration of CAR-T persistence in IP tumors after a single IP infusion and to test the therapeutic effect of multiple CAR-T infusions.

The duration of CAR-T persistence in IP tumors after a single IP infusion is determined using the mouse model described in Example 3. Using an optimal dose as determined in Example 3, ten mice with established MC38 IP tumors are treated with an IP infusion of the specific CAR-T. Tumors and ascites fluid are analyzed by flow cytometry using a monoclonal antibody specific for CAR at 1, 2, 4, 7, 14, and 21 days following treatment.

Based on the duration of CAR-T persistence and the effects of the single dose of anti-CAR-T on tumor progression as determined according to Example 3, a dosing schedule for multiple CAR-T infusions is identified and used in the multiple infusion treatment regimen.

If CAR-T persistence in IP tumors is particularly short-lived (<2-3 days), a total body irradiation preconditioning strategy is employed to promote CAR-T engraftment in the host animal.

Example 11

IP CAR-T Treatment with Chemotherapeutics

IP delivery of CAR-T to patients is conducted in compliance with Good Clinical Practice guidelines. Patients first undergo a diagnostic laparoscopy in the operating room for lysis of peritoneal adhesions, disease assessment, acquisition of pre-treatment biospecimens, and placement of a peritoneal dialysis catheter. On postoperative Day 1, about $1 \times 10^{10}$ CAR-T are infused in 200 ml normal saline (NS) with 10% dimethyl sulfoxide (DMSO). The infusion is carried out by manual injection at the bedside over a 15 minute period with continuous vital sign monitoring. Two additional CAR-T doses of $1 \times 10^{10}$ cells are given at 1-week intervals.

Six weeks following the first CAR-T dose, the patient is returned to the operating room for a diagnostic laparoscopy to assess disease response and to acquire post-treatment biospecimens.

Example 12

IP CAR-T Treatment with Chemotherapeutics

Effects of the chemotherapeutic agent cyclophosphamide on therapeutic efficacy of CAR-T cells in the mouse model are studied using methods similar to those described above. C57BL/6 mice are injected intraperitoneally with $2.5 \times 10^6$ tumor cells. Seven days after this injection, the mice receive IP injections of CAR-T cells generated as described in Example 1. Mice also receive IP injections of cyclophosphamide. The cyclophosphamide is administered 1 day prior to CAR-T infusion and then every 2 days after CAR-T administration for a total of 4 doses of the antibody. A control group of mice receive saline injection via the same dosing schedule relative to the CAR-T infusion. Efficacy of each treatment is measured by measuring bioluminescence and survival of the mice.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method of treating a peritoneal cancer in a subject, comprising: infusing into the abdominal cavity of the subject a composition comprising a substantially pure population of genetically engineered T cells which express a chimeric ligand T cell receptor protein comprising anti-CEA scfv-CD28/CD3ζ (tandem) chimeric antigen receptor (CAR), wherein the chimeric ligand T cell receptor protein binds to an antigen expressed on malignant cells.

2. The method of claim 1, wherein the malignant cells are present in the abdominal cavity.

3. The method of claim 1, wherein the malignant cells are present outside of the abdominal cavity.

4. The method of claim 1, further comprising infusing a second therapeutic agent into the abdominal cavity of the subject.

5. The method of claim 4, wherein the infusing the second therapeutic agent is performed before, during or after the infusion of the composition comprising the genetically engineered T cells.

6. The method of claim 4, wherein the second therapeutic agent is an inhibitor of GM-CSF, STAT3, PD-1, PD-L1, IL10 or TGFβ activity.

7. The method of claim 1, wherein the composition is infused into the abdominal cavity of the subject once every 1 week, once every 2 weeks, once every 3 weeks, or once every 4 weeks.

8. The method of claim 1, wherein the infusing into the abdominal cavity of the subject the composition comprises infusing $10^6$-$10^{11}$ genetically engineered T cells.

9. The method of claim 1, wherein the infusing the composition results in a decrease in the number and/or size of peritoneal tumors, abdominal ascites, peritoneal mucin, and/or serum tumor marker levels.

10. The method of claim 1, wherein the subject is human.

11. The method of claim 1, wherein the anti-CEA CAR construct comprises the amino acid sequence of SEQ ID NO: 1.

* * * * *